(12) United States Patent
Lee et al.

(10) Patent No.: US 12,740,765 B2
(45) Date of Patent: Sep. 22, 2026

(54) ULTRASOUND REMOTE DIAGNOSIS SYSTEM AND METHOD THEREOF

(71) Applicant: SAMSUNG MEDISON CO., LTD., Gangwon-do (KR)

(72) Inventors: Seung Ju Lee, Gangwon-do (KR); Hyo Ju Yeo, Gangwon-do (KR); Ga Won Choi, Gangwon-do (KR); Doo Young Na, Gangwon-do (KR); Dae Hwan Kim, Gangwon-do (KR); Ji Hye Seo, Gangwon-do (KR); Jong Rip Lee, Gangwon-do (KR); Hyug Rae Cho, Gangwon-do (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 33 days.

(21) Appl. No.: 18/116,109

(22) Filed: Mar. 1, 2023

(65) Prior Publication Data

US 2024/0008851 A1 Jan. 11, 2024

(30) Foreign Application Priority Data

Jul. 6, 2022 (KR) ........................ 10-2022-0083416
Sep. 23, 2022 (KR) ........................ 10-2022-0121199

(51) Int. Cl.
*A61B 8/00* (2006.01)

(52) U.S. Cl.
CPC ............ *A61B 8/465* (2013.01); *A61B 8/4427* (2013.01); *A61B 8/469* (2013.01); *A61B 8/54* (2013.01)

(58) Field of Classification Search
CPC ....... A61B 8/465; A61B 8/4427; A61B 8/469; A61B 8/54
See application file for complete search history.

(56) References Cited

U.S. PATENT DOCUMENTS 9,033,879 B2 5/2015 Urness et al.
9,092,556 B2 7/2015 Amble
(Continued)

FOREIGN PATENT DOCUMENTS

CN 109920527 A 6/2019
CN 110731797 A 1/2020
(Continued)

OTHER PUBLICATIONS

US 10,617,385 B2, 04/2020, Ryu et al. (withdrawn)
(Continued)

*Primary Examiner* — Dixomara Vargas
(74) *Attorney, Agent, or Firm* — Morgan Lewis & Bockius LLP

(57) ABSTRACT

An ultrasound remote diagnosis system according to an embodiment of the present disclosure includes a main body including a main panel, a touch panel, and a control panel, and a remote device in communication with the main body, wherein the remote device is configured to: independently receive, among display data which is real-time image information of the main panel, first control data which is real-time image information of the touch panel, and second control data which is a virtual control panel corresponding to the control panel, at least each information corresponding to the display data and the first control data, from the main body; and in order for manipulation information by any one of the control panel and the second controller to be displayed on the other one, the manipulation information is transmitted mutually between the main body and the remote device.

13 Claims, 33 Drawing Sheets

(56) References Cited

U.S. PATENT DOCUMENTS

| | | | | |
|---|---|---|---|---|
| 10,631,834 | B2 | 4/2020 | Kim | |
| 10,646,199 | B2 | 5/2020 | Pelissier et al. | |
| 10,860,053 | B2 | 12/2020 | Lee et al. | |
| 10,959,702 | B2 | 3/2021 | Nouri et al. | |
| 11,133,944 | B2 | 9/2021 | Yang et al. | |
| 11,298,108 | B2 | 4/2022 | Kang et al. | |
| 11,464,484 | B2 | 10/2022 | Lemaitre et al. | |
| 11,484,290 | B2 | 11/2022 | McLaughlin | |
| 2016/0157825 | A1* | 6/2016 | Lee | A61B 8/5207 600/437 |
| 2017/0065361 | A1* | 3/2017 | Kurita | A61B 5/026 |
| 2017/0347056 | A1* | 11/2017 | Kurita | A61B 8/5207 |
| 2018/0046846 | A1* | 2/2018 | Yang | A61B 8/00 |
| 2018/0344286 | A1 | 12/2018 | Mienkina et al. | |
| 2019/0261957 | A1 | 8/2019 | Zaslavsky et al. | |
| 2019/0365356 | A1 | 12/2019 | Kurita et al. | |
| 2020/0330073 | A1 | 10/2020 | McLaughlin | |
| 2023/0371927 | A1* | 11/2023 | Kim | A61B 8/4427 |
| 2024/0008850 | A1* | 1/2024 | Lee | A61B 8/464 |
| 2024/0008852 | A1* | 1/2024 | Lee | G16H 40/67 |

FOREIGN PATENT DOCUMENTS

| | | | |
|---|---|---|---|
| EP | 833266 | B1 | 7/2007 |
| JP | 2005-058574 | A | 3/2005 |
| JP | 4686168 | B2 | 5/2011 |
| JP | 6059789 | B1 | 1/2017 |
| KR | 10-2009-0116849 | A | 1/2009 |
| KR | 10-1747305 | B1 | 6/2017 |
| KR | 10-2019-0056714 | A | 5/2019 |
| KR | 10-2019-0080247 | A | 7/2019 |
| KR | 10-2116517 | B1 | 5/2020 |
| KR | 10-2184277 | B1 | 11/2020 |
| KR | 10-2218295 | B1 | 2/2021 |
| WO | 2017/081991 | A1 | 5/2017 |
| WO | 2022/044404 | A1 | 3/2022 |

OTHER PUBLICATIONS

Extended European Search Report dated Dec. 1, 2023 issued in European Patent Application No. 23160079.2.

"Wisonic wiCloud Telemedicine Technology," Shenzhen Wisonic Medical Technology, Remote Solution, May 25, 2020, https://youtu.be/sqBaz28Vb6Q.

"Release News," SonoSync, Sep. 30, 2021.

"Pre-RSNA Meeting," SonoSync, Nov. 27, 2021.

RSBA 2021 System Introduction, RS85 Prestige, V+, HM70 EVO, and SonoSync.

"User Manual," SonoSync.

Office Action dated Mar. 14, 2025 issued in corresponding European Patent Application No. 23160079.2.

European Notice of Allowance dated May 26, 2026 issued in European Patent Application No. 23160079.2.

* cited by examiner 100
130
Image processor
140
Display unit
150
Storage
120
Controller
160
Communication unit
110
116b
Digital beamformer
116a
Analog beamformer
Input unit
170
20
Probe
10

ULTRASOUND REMOTE DIAGNOSIS SYSTEM AND METHOD THEREOF

CROSS-REFERENCE TO RELATED APPLICATION

The present application claims priority under 35 U.S.C. § 119(a) to Korean patent application number 10-2022-0083416 filed on Jul. 6, 2022, and 10-2022-0121199 filed on Sep. 23, 2022 in the Korean Intellectual Property Office, the entire disclosure of which is incorporated by reference herein.

BACKGROUND

1. Technical Field

The present disclosure relates to an ultrasound remote diagnosis system and an ultrasound remote diagnosis method, and more particularly, to an ultrasound diagnosis system and a diagnosis method method capable of remotely diagnosing ultrasound.

2. Related Art

Ultrasound imaging refers to imaging of sound waves reflected from the inside of a human body after sending high-frequency sound waves from a surface of the human body to the inside and the ultrasound examination provides ultrasound images in real time. Conventionally, an ultrasound diagnosis apparatus is being changed from an analog type to a digital type as well as from 2D ultrasound diagnosis apparatuses to 3D and then 4D ultrasound diagnosis apparatuses that include the passage of time, and recently, 4D ultrasound examination is also being applied, which shows the movement of 3D images.

The ultrasound diagnosis apparatus is an apparatus which irradiates ultrasound signals generated from a transducer of a probe to an object and receives information of echo signals reflected from the object to acquire an image of an internal part of the object, and such an ultrasound diagnosis apparatus exhibits higher stability than a diagnosis apparatus using X-rays while the real-time image display is possible, thereby being widely used along with other imaging diagnosis apparatuses. In particular, ultrasound diagnosis apparatuses, which are more accurate than other diagnosis apparatuses and are safe due to no risk of radiation exposure to the human body, are widely used in various diagnostic processes.

With the development of ultrasound remote diagnosis technology, it has become possible to diagnose or treat bedside at a remote location, and recently, ultrasound remote diagnosis technology has been used in the training process of ultrasound apparatuses.

SUMMARY

Embodiments provide an ultrasound remote diagnosis system and a diagnosis method that facilitate remote diagnosis by improving operational inconvenience in the ultrasound remote diagnosis process and increase the accuracy of diagnosis.

In accordance with an aspect of the present disclosure, there is provided an ultrasound remote diagnosis system, including a remote device in communication with a main body including a main panel, a touch panel, and a control panel, wherein the remote device is configured to: independently receive, among display data which is real-time image information of the main panel, first control data which is real-time image information of the touch panel, and second control data which is a virtual control panel corresponding to the control panel, at least each information corresponding to the display data and the first control data, from the main body; and display a display part, a first controller, and a second controller respectively corresponding to the display data, the first control data, and the second control data so as not to overlap, and wherein in order for manipulation information by any one of the control panel and the second controller to be displayed on the other one, the manipulation information is transmitted mutually between the main body and the remote device.

In accordance with another aspect of the present disclosure, there is provided an ultrasound remote diagnosis system, including a main body in communication with a remote device, wherein the main body includes a main panel, a touch panel, and a control panel, and in order for the remote device to display a display part, a first controller, and a second controller respectively corresponding to display data which is real-time image information of the main panel, first control data which is real-time image information of the touch panel, and second control data which is a virtual control panel corresponding to the control panel, so as not to overlap, the main body is configured to independently transmit, among the display data, the first control data and the second control data, at least each information corresponding to the display data and the first control data, to the remote device, and wherein in order for manipulation information by any one of the control panel and the second controller to be displayed on the other one, the manipulation information is transmitted mutually between the main body and the remote device.

In accordance with another aspect of the present disclosure, there is provided an ultrasound remote diagnosis system, including a main body including a main panel, a touch panel, and a control panel, and a remote device in communication with the main body, wherein the remote device is configured to: independently receive, among display data which is real-time image information of the main panel, first control data which is real-time image information of the touch panel, and second control data which is a virtual control panel corresponding to the control panel, at least each information corresponding to the display data and the first control data, from the main body; and display a display part, a first controller, and a second controller respectively corresponding to the display data, the first control data, and the second control data so as not to overlap, and wherein in order for manipulation information by any one of the control panel and the second controller to be displayed on the other one, the manipulation information is transmitted mutually between the main body and the remote device.

Specifically, the manipulation information by the control panel may be displayed on the second controller in real time, and the manipulation information by the second controller may be displayed on the control panel in real time.

Specifically, the manipulation information by the control panel displayed on the second controller may be displayed as a GUI.

Specifically, the remote device capable of remotely accessing the main body may be at least one.

Specifically, manipulation information of a plurality of the second controllers may be respectively displayed mutually between the plurality of second controllers.

Specifically, a plurality of pieces of manipulation information displayed on the second controller may be displayed in mutually distinguished forms.

Specifically, manipulation information of a plurality of the second controllers may be respectively displayed on the control panel.

Specifically, a plurality of pieces of manipulation information displayed on the control panel may be displayed in mutually distinguished forms.

Specifically, the manipulation information displayed on the control panel may be displayed in a blinking manner of a control panel manipulator.

Specifically, the manipulation information by the control panel and the manipulation information by the second controller, displayed on the control panel, may be displayed in mutually distinguished forms.

Specifically, the touch panel and the first controller, and the control panel and the second controller may each independently perform two-way transmission and reception.

In accordance with another aspect of the present disclosure, there is provided an ultrasound remote diagnosis method of an ultrasound remote diagnosis system including a main body including a main panel, a touch panel, and a control panel, and a remote device in communication with the main body, the method including independently receiving, by the remote device, among display data which is real-time image information of the main panel, first control data which is real-time image information of the touch panel, and second control data which is a virtual control panel corresponding to the control panel, at least each information corresponding to the display data and the first control data, from the main body, displaying, by the remote device, a display part, a first controller, and a second controller respectively corresponding to the display data, the first control data, and the second control data so as not to overlap, and in order for manipulation information by any one of the control panel and the second controller to be displayed on the other one, mutually transmitting the manipulation information between the main body and the remote device.

Specifically, the method may include displaying the manipulation information by the control panel on the second controller in real time. Specifically, the method may include displaying the manipulation information by the second controller on the control panel in real time.

Specifically, the manipulation information by the control panel displayed on the second controller may be displayed as a GUI.

Specifically, the remote device capable of remotely accessing the main body may be at least one.

Specifically, manipulation information of a plurality of the second controllers may be respectively displayed mutually between the plurality of second controllers.

Specifically, a plurality of pieces of manipulation information displayed on the second controller may be displayed in mutually distinguished forms.

Specifically, manipulation information of a plurality of the second controllers may be respectively displayed on the control panel.

Specifically, a plurality of pieces of manipulation information displayed on the control panel may be displayed in mutually distinguished forms.

Specifically, the manipulation information displayed on the control panel is displayed in a blinking manner of a control panel manipulator.

Specifically, the manipulation information by the control panel and the manipulation information by the second controller, displayed on the control panel, may be displayed in mutually distinguished forms.

Specifically, the touch panel and the first controller, and the control panel and the second controller may each independently perform two-way transmission and reception.

An ultrasonic remote diagnosis system and diagnostic method according to the present disclosure may allow an operation process in the main body ultrasound equipment to be checked in a remote device during the ultrasonic remote diagnosis process, thereby improving the usability of remote control.

The effect of the present disclosure is not limited to the above-mentioned effects, and effects not mentioned may be clearly understood by those skilled in the art to which the present disclosure pertains from the present specification and the accompanying drawings.

BRIEF DESCRIPTION OF THE DRAWINGS

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey the scope of the example embodiments to those skilled in the art.

In the drawing figures, dimensions may be exaggerated for clarity of illustration. It will be understood that when an element is referred to as being "between" two elements, it can be the only element between the two elements, or one or more intervening elements may also be present. Like reference numerals refer to like elements throughout.

FIGS. 4A to 4C are perspective views of an ultrasound diagnosis apparatus 200 in accordance with at least one embodiment of the present disclosure.

FIGS. 9B to 9C are a diagram for explaining a process of executing the measurement mode of the ultrasound remote diagnosis system 700 in accordance with an embodiment of the present disclosure.

FIG. 13 is a diagram for explaining a display method of the ultrasound remote diagnosis system 700 in accordance with an embodiment of the present disclosure.

FIG. 14 is a diagram for explaining a display method of the ultrasound remote diagnosis system 700 in accordance with an embodiment of the present disclosure.

FIG. 18 is a diagram for explaining a method of controlling the remote track ball 727, in the remote track ball 727 control method of the ultrasound remote diagnosis system 700 in accordance with the present disclosure.

FIG. 21A is a diagram for explaining the second controller 726, in the remote track ball 727 control method of the ultrasound remote diagnosis system 700 in accordance with an embodiment of the present disclosure.

DETAILED DESCRIPTION

Figure 1:
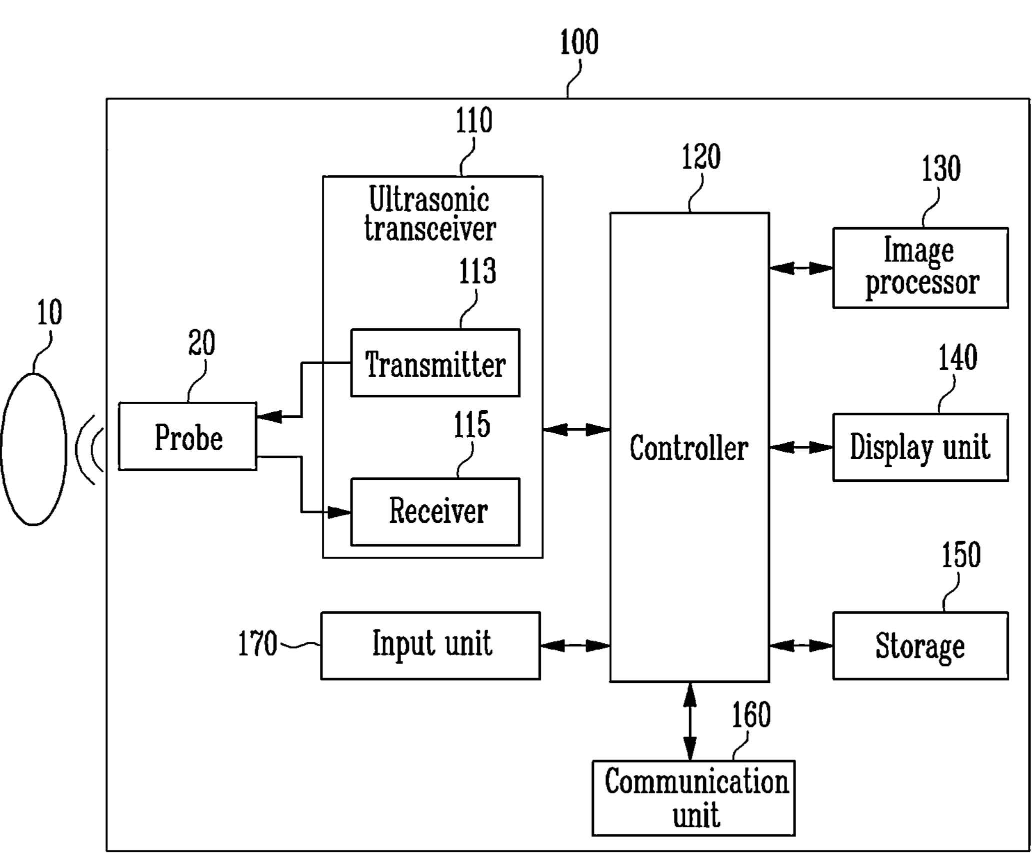
FIG. 1 is a block diagram illustrating a configuration of an ultrasound diagnosis apparatus 100 in accordance with any one embodiment of the present disclosure.

The present specification clarifies the scope of the present disclosure and, to enable those of ordinary skill in the art to which the present disclosure pertains to practice the present disclosure, the principle of the present disclosure is explained and embodiments are disclosed. The disclosed embodiments may be implemented in various forms.

Throughout the specification, when a part is "connected" to another part, it includes not only a case of being directly connected but also a case of being indirectly connected, and the indirect connection includes connection through a wireless communication network.

In addition, terms used herein are used to describe the embodiments, not intended to limit and/or restrict the disclosed invention. The singular expression includes the plural expression unless the context clearly dictates otherwise. In the present specification, terms such as "comprise" or "have" specify the presence of stated features, integers, steps, operations, elements, components or a combination thereof, but do not preclude the presence or addition of one or more other features, integers, steps, operations, elements, components, a combination thereof.

Further, although terms including ordinal numbers such as "first," "second," and the like are used to explain various components, the components are not limited to such terms and these terms are used only to distinguish one component from another component. For example, a first component may be referred to as a second component, or similarly, the second component may be referred to as the first component within the scope of the present disclosure.

In addition, terms such as "unit", "group", "block", "member", and "module" may refer to a unit that processes at least one function or operation. For example, the terms may refer to at least one process processed by at least one hardware such as a field-programmable gate array (FPGA)/application specific integrated circuit (ASIC), at least one software stored in a memory, or a processor.

Symbols given to each step are used to identify each step, and these signs do not indicate the order between the steps, and each step may be performed differently from the stated order unless the context clearly indicates a specific order.

In addition, an image herein may include a medical image acquired by a medical imaging apparatus such as a magnetic resonance imaging (MRI) apparatus, a computed tomography (CT) apparatus, an ultrasound imaging apparatus, or an X-ray imaging apparatus, and ultrasound images and medical images of other modalities other than ultrasound may be provided or controlled.

Further, the term 'object' as used herein refers to a subject to be photographed, and may include human, animal, or a part thereof. For example, the object may include a part of the body (such as organs) or a phantom.

Throughout the specification, the term "ultrasound image" as used herein refers to an image for an object transmitted to the object and processed based on an ultrasound signal reflected from the object.

Hereinafter, an embodiment according to the present disclosure will be described in detail with reference to the accompanying drawings.

FIG. 1 is a block diagram illustrating a configuration of an ultrasound diagnosis apparatus 100 in accordance with any one embodiment of the present disclosure.

The ultrasound diagnosis apparatus 100 according to an embodiment of the present disclosure may include a probe 20, an ultrasonic transceiver 110, a controller 120, an image processor 130, a display unit 140, a storage 150, a communication unit 160, and an input unit 170.

The ultrasound diagnosis apparatus 100 may be provided not only as a cart type but also as a portable type. Examples of the portable ultrasound diagnosis apparatus may include a smart phone, a laptop computer, a PDA, and a tablet PC including a probe and an application, but are not limited thereto.

The probe 20 may include a plurality of transducers. The plurality of transducers may transmit an ultrasound signal to an object 10 according to a transmission signal applied from a transmitter 113. The plurality of transducers may be configured to receive the ultrasound signal reflected from the object 10 to generate a received signal. In addition, the probe 20 may be integrated with the ultrasound diagnosis apparatus 100 or may be provided as a separate type connected to the ultrasound diagnosis apparatus 100 by a wire or wirelessly. Moreover, the ultrasound diagnosis apparatus 100 may include one or a plurality of probes 20 according to an implementation form.

The controller 120 is configured to control, in consideration of the position and focal point of the plurality of transducers included in the probe 20, the transmitter 113 to generate a transmission signal to be applied to each of the plurality of transducers.

The controller 120 is configured to convert the received signal received from the probe 20 from analog to digital and, in consideration of the positions and focal points of the plurality of transducers, add the digitally converted received signals to control the receiver 115 to generate ultrasound data.

The image processor 130 is configured to generate an ultrasound image by using the ultrasound data generated by the ultrasound receiver 115.

Meanwhile, the ultrasound image may represent the motion of the object as a Doppler image as well as a gray scale ultrasound image obtained by scanning the object according to the A mode (amplitude mode), the B mode (brightness mode), and the M mode (motion mode).

A-mode is the most basic form of ultrasound image display method, which is a method that displays the intensity of the reflected sound as the amplitude size on the time (distance) axis, and if the reflected sound is strong, the amplitude is high, and if the reflected sound is weak, the amplitude is low, which is advantageous for distance measurement, but this mode is rarely used at present because the image changes even if the direction of the probe is slightly changed.

M-mode is a mode in which the distance of the moving reflector is displayed as a temporal change in the changed form of A-mode. By specifying the region of interest (ROI) in the 2D image as an M line and displaying the change over time in that area, it is mainly used to observe heart valves, and may also record fetal heart sounds, but has recently been replaced by the Doppler method.

B-mode is a method of displaying the reflected sound as the brightness of a dot, which is currently used in most ultrasound diagnostic equipment, and the brightness of each dot is proportional to the amplitude of the reflected signal, and recently provides a brightness level of 256 or more, and is also a mode in which long-term motions are visualized and displayed as they are in real time. The mode called 2D mode, which means B (brightness) mode, displays the cross-sectional image of an object in real time on the screen in black and white shades, and is the most used mode.

In addition, the Doppler mode is a mode that measures blood flow by detecting the flow of red blood cells in blood vessels in general, which uses the principle that the wavelength shortens when red blood cells approach the probe and lengthens when they move away, and there are color Doppler, pulse wave Doppler (PW), continuous wave Doppler (CW), etc., according to the method of displaying blood flow. The Doppler image may include a blood flow Doppler image showing blood flow (also called color Doppler image), a tissue Doppler image showing tissue movement and a spectral Doppler image displaying the moving speed of the object in a waveform.

In addition, as a composite mode, there are a mode in which two or three modes are simultaneously applied to one image to display other modes based on 2D, and a 3D mode in which a 3D stereoscopic image is displayed.

In the B-mode processing process, B-mode components are extracted and processed from ultrasound data, and in the image generation process, an ultrasound image in which signal intensity is expressed as brightness may be generated based on the B mode component extracted in the B mode processing process. In the Doppler processing process, Doppler components are extracted from ultrasound data, and in the image generation process, a Doppler image expressing the motion of the object in color or waveform may be generated based on the extracted Doppler component.

In the image generation process, a 2D ultrasound image or a 3D image of the object may be generated, and an elastic image obtained by imaging the degree of deformation of the object according to pressure may also be generated. Furthermore, various types of additional information may be expressed as text or graphics on the ultrasound image. Meanwhile, the generated ultrasound image may be stored in a memory.

In the process of measuring the object in the ultrasound image, a measurement tool for measuring the object may be determined, and one of a plurality of measurement tools may be selected based on a user input.

For example, a measurement tool selection menu for selecting one of the plurality of measurement tools may be provided, and the measurement tool selection menu may be displayed on one screen together with the ultrasound image. In addition, the measurement tool selection menu may be displayed on a separate screen different from the touch screen on which the ultrasound image is displayed.

In addition, one of the plurality of measurement tools may be determined based on a user input for selecting one of the plurality of measurement items to be measured. The measurement item may include, but is not limited to, length, width, or angle.

As a user input for selecting one of the measurement items is received, a predetermined measurement tool may be determined corresponding to the selected measurement item.

The display unit 140 may be configured to display the generated ultrasound image and various information processed in the ultrasound diagnosis apparatus 100. The ultrasound diagnosis apparatus 100 may include one or a plurality of display units 140 according to an implementation form. In addition, the display unit 140 may be provided as a touch screen in combination with a touch panel.

The controller 120 may control the overall operation of the ultrasound diagnosis apparatus 100 and a signal flow between internal components of the ultrasound diagnosis apparatus 100. The controller 120 may include a memory configured to store a program or data for performing a function of the ultrasound diagnosis apparatus 100, and a processor configured to process a program or data. In addition, the controller 120 may be configured to receive a control signal from the input unit 170 or an external device to control the operation of the ultrasound diagnosis apparatus 100.

The ultrasound diagnosis apparatus 100 may include the communication unit 160 and be connected with an external device (e.g., a server, a medical device, a portable device (smartphones, tablet PCs, wearable devices, etc.)) through the communication unit 160.

The communication unit 160 may include one or more components that enable communication with the external device, including, for example, at least one of short-range communication modules, wired communication modules, and wireless communication modules.

It is also possible that the communication unit 160 receives a control signal and data from the external device and transmits the received control signal to the controller 120 so as to have the controller 120 control the ultrasound diagnosis apparatus 100 according to the received control signal.

Alternatively, it is also possible that the controller 120 transmits a control signal to the external device through the communication unit 160 to control the external device in accordance with the control signal of the controller.

For example, the external device may be configured to process data of the external device in accordance with the control signal of the controller received through the communication unit.

A program (such as artificial intelligence) capable of controlling the ultrasound diagnosis apparatus 100 may be installed in the external device, such that the program may include instructions for performing some or all of the operations of the controller 120.

The program may be preinstalled in the external device or may be installed by downloading, by a user of the external device, the program from a server that provides an application. The server providing the application may include a recording medium in which the corresponding program is stored.

In addition, the program may include a storage medium of a server or a storage medium of a client device in a system consisting of a server and a client device. Alternatively, if there is a third device (smartphones, tablet PCs, wearable devices, etc.) that is communicatively connected to the server or client device, the program product may include a storage medium of the third device. Alternatively, the program may include a S/W program itself transmitted from the server to the client device or the third device, or transmitted from the third device to the client device.

In this case, one of the server, the client device, and the third device may execute the program to perform methods according to the disclosed embodiments. Alternatively, two or more of the server, the client device, and the third device may execute the program to perform the methods according to the disclosed embodiments by distributing the methods.

For example, a server (e.g., a cloud server or an artificial intelligence server, etc.) may execute a program stored in the server, so as to control the client device that is communicatively connected to the server to perform the method according to the disclosed embodiments.

The storage 150 may be configured to store various data or programs for driving and controlling the ultrasound diagnosis apparatus 100, input/output ultrasound data, and an acquired ultrasound image.

The input unit 170 may be configured to receive a user input for controlling the ultrasound diagnosis apparatus 100. For example, the user input may include an input for manipulating a button, a keypad, a mouse, a trackball, a jog switch, a knob, etc., an input for touching a touch pad or a touch screen, a voice input, a motion input, and an input of biometric information (e.g., iris recognition, fingerprint recognition, etc.), but is not limited thereto.

Figure 2:
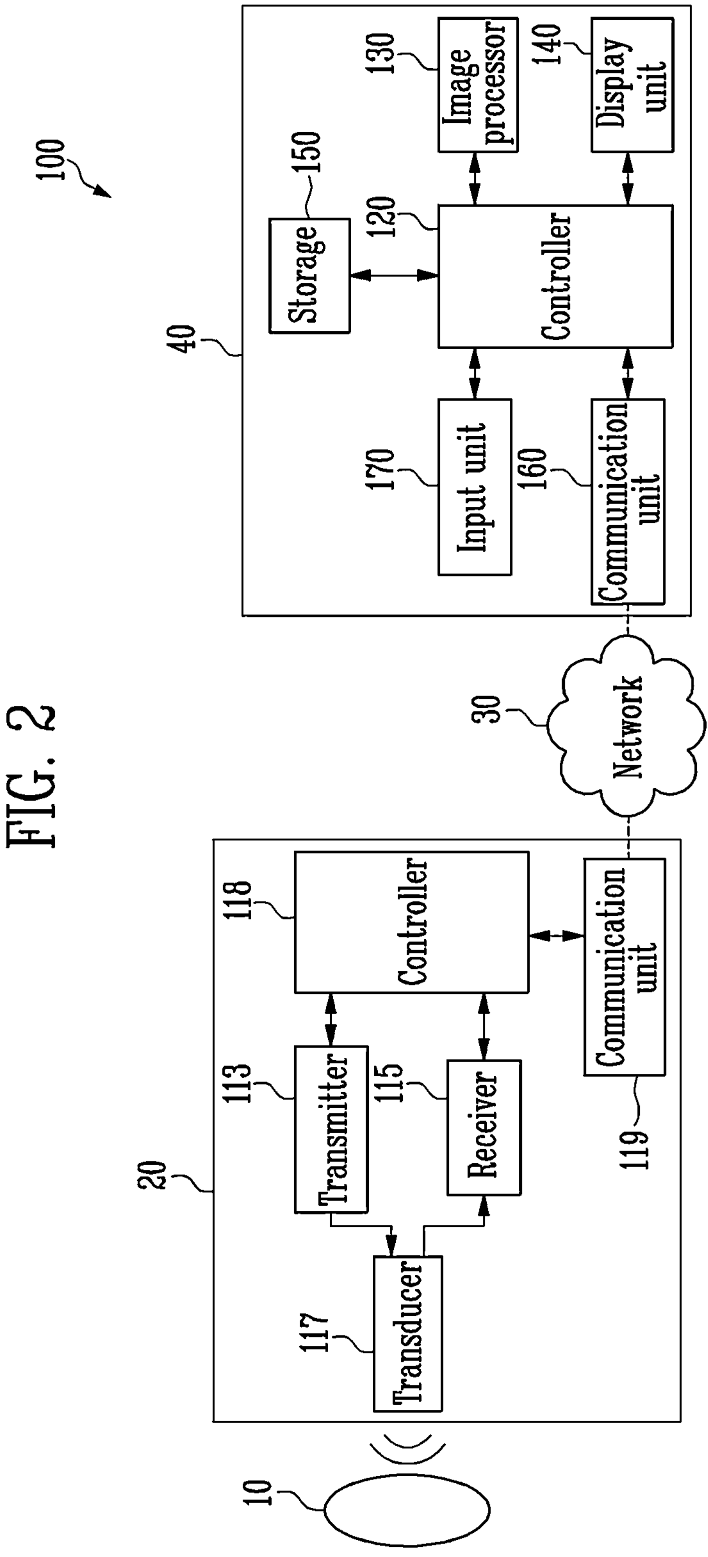
FIG. 2 is a block diagram illustrating a configuration of the ultrasound diagnosis apparatus 100 in accordance with any one embodiment of the present disclosure.

FIG. 2 is a block diagram illustrating a configuration of the ultrasound diagnosis apparatus 100 in accordance with any one embodiment of the present disclosure.

Referring to FIG. 2, the ultrasound diagnosis apparatus 100 may include a wireless probe 20 and an ultrasound system 40.

The wireless probe 20 may include the transmitter 113, a transducer 117, a receiver 115, a controller 118, and a communication unit 119. It is shown in FIG. 2 that the wireless probe 20 includes both the transmitter 113 and the receiver 115, but depending on the implementation, the wireless probe 20 may include only a part of the configuration of the transmitter 113 and the receiver 115, and a part of the configuration of the transmitter 113 and the receiver 115 may be included in the ultrasound system 40. Alternatively, the wireless probe 20 may further include the image processor 130.

The transducer 117 may include a plurality of transducers. The plurality of transducers may be configured to transmit an ultrasound signal to the object 10 according to a transmission signal transmitted from the transmitter 113. The plurality of transducers may be configured to receive the ultrasound signal reflected from the object 10 to generate a received signal.

The controller 118 is configured to control the transmitter 113 to generate a transmission signal to be transmitted to each of the plurality of transducers in consideration of the positions and focal points of the plurality of transducers.

The controller 118 is configured to convert the received signal received from the transducer 117 from analog to digital and, in consideration of the positions and focal points of the plurality of transducers, sum up the digitally converted received signals to control the receiver 155 to generate ultrasound data. Alternatively, when the wireless probe 20 includes the image processor 130, it is possible to generate an ultrasound image using the generated ultrasound data.

The communication unit 119 may be configured to wirelessly transmit the generated ultrasound data or ultrasound image to the ultrasound system 40 through a wireless network. Alternatively, the communication unit 119 may be configured to receive a control signal and data from the ultrasound system 40.

In addition, the ultrasound diagnosis apparatus 100 may include one or more wireless probes 20 according to an implementation form.

The ultrasound system 40 may be configured to receive ultrasound data or an ultrasound image from the wireless probe 20. The ultrasound system 40 may include the controller 120, the image processor 130, the display unit 140, the storage 150, the communication unit 160, and the input unit 170.

The image processor 130 may be configured to generate an ultrasound image by using the ultrasound data received from the wireless probe 20.

The display unit 140 may be configured to display an ultrasound image received from the wireless probe 20, an ultrasound image generated in the ultrasound system 40, and various information processed in the ultrasound diagnosis apparatus 100. The ultrasound diagnosis apparatus 100 may include one or a plurality of display units 140 according to an implementation form. In addition, the display unit 140 may be provided as a touch screen in combination with a touch panel.

The controller 120 may be configured to control the overall operation of the ultrasound diagnosis apparatus 100 and the signal flow among the internal components of the ultrasound diagnosis apparatus 100. The controller 120 may include a memory configured to store a program or data for performing a function of the ultrasound diagnosis apparatus 100, and a processor configured to process a program or data. Further, the controller 120 may be configured to receive a control signal from the input unit 170 or an external device to control the operation of the ultrasound diagnosis apparatus 100.

The ultrasound system 40 may include the communication unit 160 and be connected with the external device (e.g., a server, a medical device, a portable device (smartphones, tablet PCs, wearable devices, etc.)) through the communication unit 160.

The communication unit 160 may include one or more components that enable communication with the external device, including, for example, at least one of short-range communication modules, wired communication modules and wireless communication modules.

It is also possible that the communication unit 160 transmits and receives a control signal and data from the external device and transmits the received control signal to the controller 120 so as to have the controller 120 control the ultrasound diagnosis apparatus 100 according to the received control signal.

Alternatively, it is also possible that the controller 120 transmits a control signal to the external device through the communication unit 160 to control the external device in accordance with the control signal of the controller.

For example, the external device may be configured to process data of the external device in accordance with the control signal of the controller received through the communication unit.

A program (such as artificial intelligence) capable of controlling the ultrasound diagnosis apparatus 100 may be installed in the external device, such that the program may include instructions for performing some or all of the operations of the controller 120.

The program may be preinstalled in the external device or may be installed by downloading, by a user of the external device, the program from a server that provides an application. The server providing the application may include a recording medium in which the corresponding program is stored.

In addition, the program may include a storage medium of a server or a storage medium of a client device in a system consisting of a server and a client device. Alternatively, if there is a third device (smartphones, tablet PCs, wearable devices, etc.) that is communicatively connected to the server or client device, the program product may include a storage medium of the third device. Alternatively, the program may include a S/W program itself transmitted from the server to the client device or the third device, or transmitted from the third device to the client device.

In this case, one of the server, the client device, and the third device may execute the program to perform the methods according to the disclosed embodiments. Alternatively, the client device may perform the method according to the disclosed embodiments via the server.

Alternatively, two or more of the server, the client device, and the third device may execute the program for perform the methods according to the disclosed embodiments by distributing the methods.

For example, a server (e.g., a cloud server or an artificial intelligence server, etc.) may be configured to execute a program stored in the server, so as to control the client device that is communicatively connected to the server to perform the methods according to the disclosed embodiments.

The storage 150 may be configured to store various data or programs for driving and controlling the ultrasound diagnosis apparatus 100, input/output ultrasound data, and an ultrasound image.

The input unit 170 may be configured to receive a user input for controlling the ultrasound diagnosis apparatus 100. For example, the user input may include an input for manipulating a button, a keypad, a mouse, a trackball, a jog switch, a knob, etc., an input for touching a touch pad or a touch screen, a voice input, a motion input, and an input of biometric information (e.g., iris recognition, fingerprint recognition, etc.), but is not limited thereto.

Figure 3:
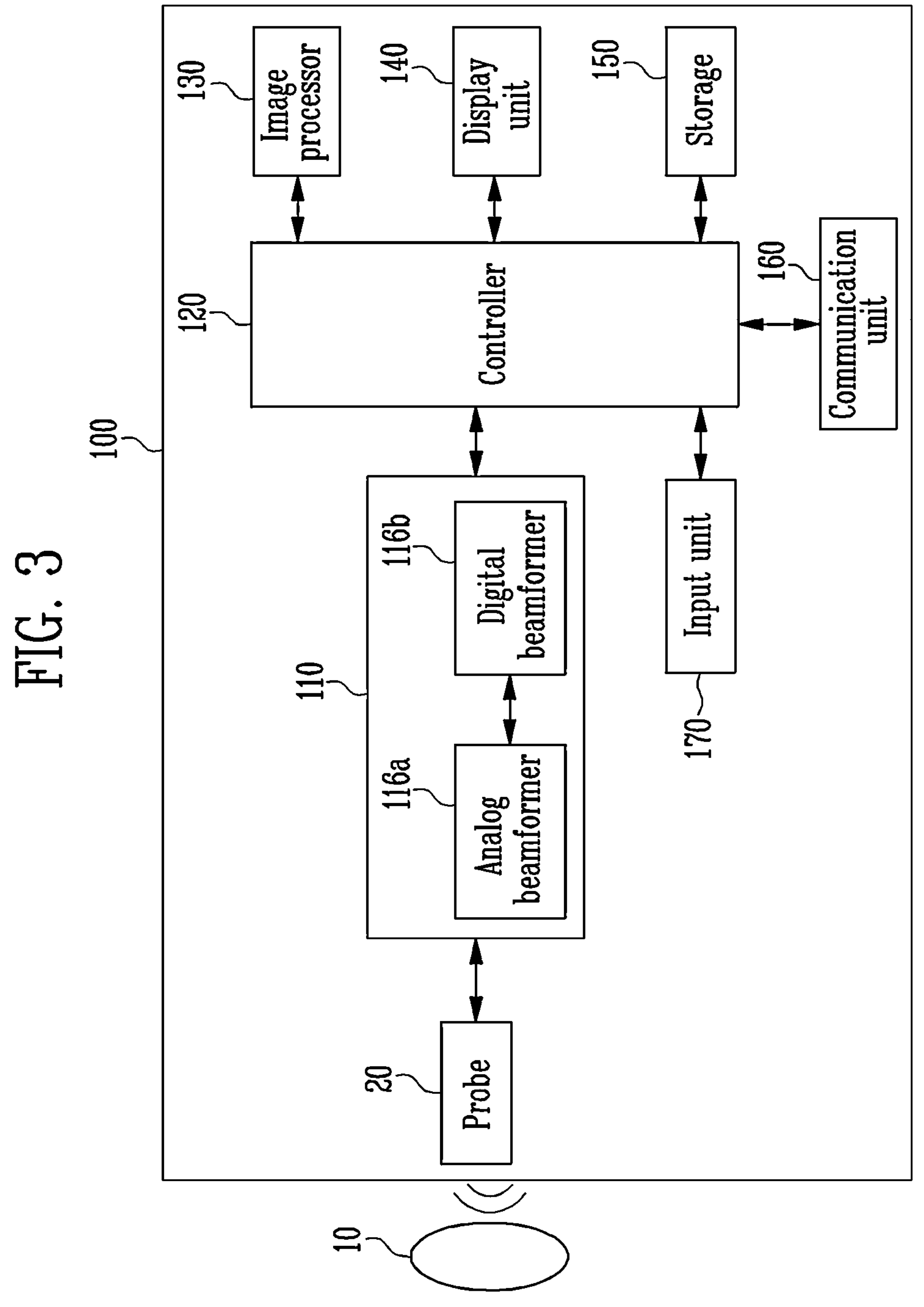
FIG. 3 is a block diagram illustrating a configuration of the ultrasound diagnosis apparatus 100 in accordance with any one embodiment of the present disclosure.

FIG. 3 is a block diagram illustrating a configuration of the ultrasound diagnosis apparatus 100 in accordance with any one embodiment of the present disclosure.

Referring to FIG. 3, the ultrasound diagnosis apparatus 100 may include a probe 20, an ultrasonic transceiver 110, a controller 120, an image processor 130, a display unit 140, an input unit 170, a storage 150, and a communication unit 160.

The probe 20 according to an embodiment of the present disclosure may include a plurality of transducers. The plurality of transducers may be arranged in two dimensions to form a 2D transducer array.

For example, the 2D transducer array may have a form including a plurality of sub-arrays including a plurality of transducers arranged in a first direction and in a second direction different from the first direction.

Further, the ultrasonic transceiver 110 may include an analog beamformer **116*a* and a digital beamformer 116*b*. Though the ultrasonic transceiver 110 and the probe 20 are illustrated as having a separate configuration in FIG. 3, the probe 20 according to an embodiment of the present disclosure may include partial or entire configuration of ultrasonic transceiver 110 according to the implementation form. For example, the probe 20 may include one or both of the analog beamformer 116*a* and the digital beamformer 116*b***.

The controller 120 may be configured to calculate a time delay value for digital beamforming for each sub-array with respect to each of the plurality of sub-arrays included in the 2D transducer array. Further, the controller 120 may be configured to calculate a time delay value for analog beamforming with respect to each of the transducers included in any one of the plurality of sub-arrays.

The controller 120 may be configured to control, according to the time delay value for analog beamforming and the time delay values for digital beamforming, the analog beamformer **116*a* and the digital beamformer 116*b*** to generate a transmission signal to be transmitted to each of the plurality of transducers.

Further, the controller 120 may be configured to control the analog beamformer **116*a* to sum up the signals received from the plurality of transducers for each sub-array according to the time delay value for analog beamforming. In addition, the controller 120 may be configured to control the ultrasonic transceiver 110 to convert the signal summed for each sub-array from analog to digital. In addition, the controller 120 may be configured to control the digital beamformer 116*b*** to generate ultrasound data by summing the digitally converted signals according to the time delay value for digital beamforming.

The image processor 130 is configured to generate an ultrasound image using the generated ultrasound data.

The display unit 140 may be configured to display the generated ultrasound image and various information processed in the ultrasound diagnosis apparatus 100. The ultrasound diagnosis apparatus 100 may include one or a plurality of display units 140 according to an implementation form. In addition, the display unit 140 may be provided as a touch screen in combination with a touch panel.

The controller 120 may be configured to control the overall operation of the ultrasound diagnosis apparatus 100 and the signal flow among the internal components in the ultrasound diagnosis apparatus 100. The controller 120 may include a memory configured to store a program or data for performing a function of the ultrasound diagnosis apparatus 100 and a processor configured to process a program or data. Further, the controller 120 may be configured to receive a control signal from the input unit 170 or the external device to control the operation of the ultrasound diagnosis apparatus 100.

The ultrasound diagnosis apparatus 100 may include the communication unit 160 and be connected with the external device (e.g., a server, a medical device, a portable device (smartphones, tablet PCs, wearable devices, etc.)) through the communication unit 160.

The communication unit 160 may include one or more components that enable communication with the external device, including, for example, at least one of short-range communication modules, wired communication modules and wireless communication modules.

It is possible that the communication unit 160 receives a control signal and data from the external device and transmits the received control signal to the controller 120 so as to have the controller 120 control the ultrasound diagnosis apparatus 100 according to the received control signal.

Alternatively, it is also possible that the controller 120 transmits the control signal to the external device through the communication unit 160 to control the external device according to the control signal of the controller.

For example, the external device may be configured to process data of the external device according to the control signal of the controller received through the communication unit.

A program (such as artificial intelligence) capable of controlling the ultrasound diagnosis apparatus 100 may be installed in the external device, such that the program may include instructions for performing some or all of the operations of the controller 120.

The program may be preinstalled in the external device or may be installed by downloading, by a user of the external device, the program from a server that provides an application. The server providing the application may include a recording medium in which the corresponding program is stored.

In addition, the program may include a storage medium of a server or a storage medium of a client device in a system consisting of a server and a client device. Alternatively, if there is a third device (smartphones, tablet PCs, wearable devices, etc.) that is communicatively connected to the server or client device, the program product may include a storage medium of the third device. Alternatively, the program may include a S/W program itself transmitted from the server to the client device or the third device, or transmitted from the third device to the client device.

In this case, one of the server, the client device, and the third device may execute the program to perform the methods according to the disclosed embodiments. Alternatively, two or more of the server, the client device, and the third device may execute the program to perform the methods according to the disclosed embodiments by distributing the methods.

For example, a server (e.g., a cloud server or an artificial intelligence server, etc.) may be configured to execute a program stored in the server, so as to control the client device that is communicatively connected to the server to perform the methods according to the disclosed embodiments.

The storage 150 may be configured to store various data or programs for driving and controlling the ultrasound diagnosis apparatus 100, input/output ultrasound data, and an ultrasound image.

The input unit 170 may be configured to receive a user input for controlling the ultrasound diagnosis apparatus 100. For example, the user input may include an input for manipulating a button, a keypad, a mouse, a trackball, a jog switch, a knob, etc., an input for touching a touch pad or a touch screen, a voice input, a motion input, and an input of biometric information (e.g., iris recognition, fingerprint recognition, etc.), but is not limited thereto.

Figure 4A:
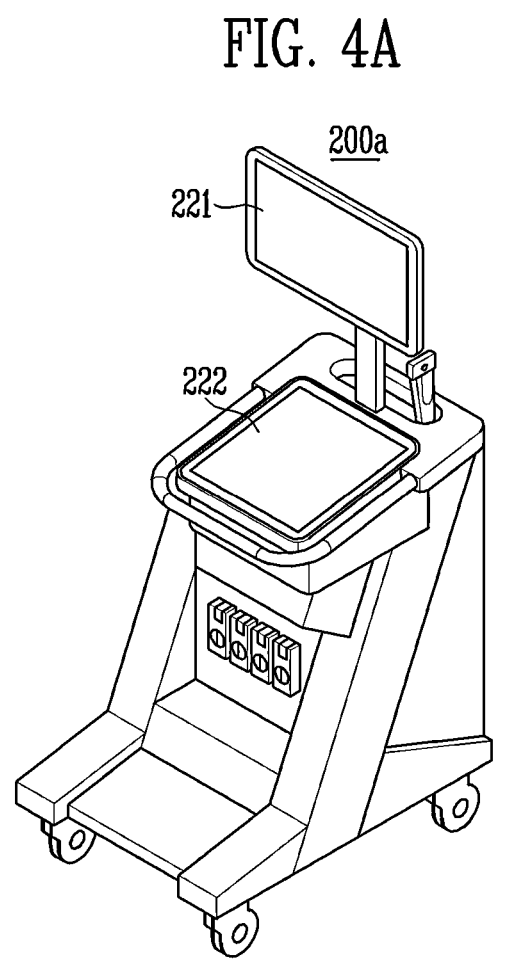
Figure 4B:
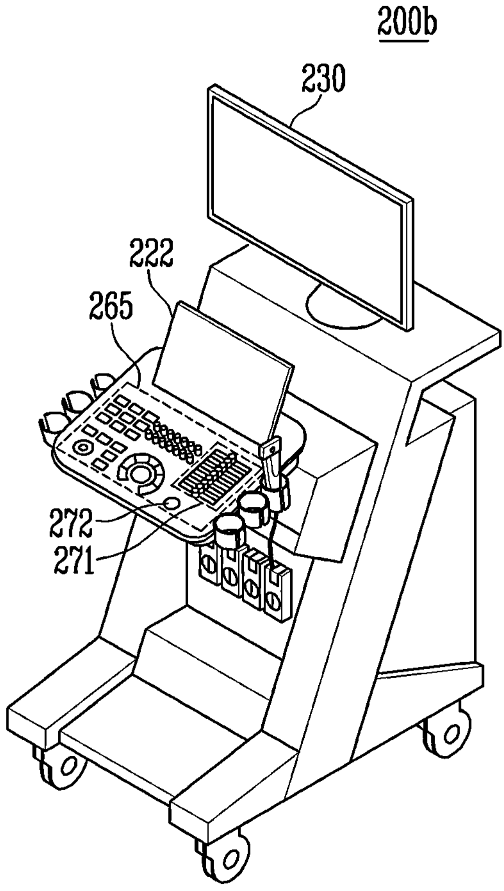
Figure 4C:
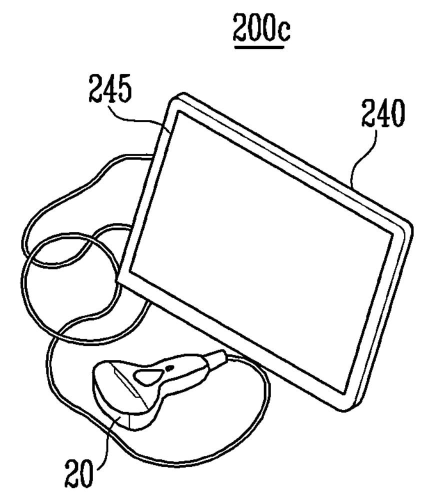

FIGS. 4A to 4C are perspective views of an ultrasound diagnosis apparatus 200 in accordance with at least one embodiment of the present disclosure.

Referring to FIGS. 4A and 4B, the ultrasound diagnosis apparatuses 200*a* and 200*b* may include a main display unit 221 and a sub-display unit 222. One of the main display unit 221 and the sub-display unit 222 may be provided as a touch screen. The main display unit 221 and the sub-display unit 222 may be configured to display an ultrasound image or various information processed in the ultrasound diagnosis apparatuses 200*a* and 200*b*. In addition, the main display unit 221 and the sub-display unit 222 may be provided as a touch screen, and by providing a GUI, data for controlling the ultrasound diagnosis apparatuses 200*a* and 200*b* may be received from a user. For example, the main display unit 221 may be configured to display an ultrasound image, and the sub-display unit 222 may be configured to display a control panel for controlling the display of the ultrasound image in the form of a GUI. The sub-display unit 222 may be input with data for controlling the display of an image through a control panel displayed in the form of a GUI. The ultrasound diagnosis apparatuses 200*a* and 200*b* may be configured to control the display of the ultrasound image displayed on the main display unit 221 by using the received control data.

Referring to FIG. 4B, the ultrasound diagnosis apparatus 200*b* may further include a control panel 265 in addition to the main display unit 221 and the sub-display unit 222. The control panel 265 may include a button, a trackball, a jog switch, and a knob, and may be input with data for controlling the ultrasound diagnosis apparatus 200*b* from a user. For example, the control panel 265 may include a time gain compensation (TGC) button 271, and a freeze button 272. The TGC button 271 is a button for setting a TGC value for each depth of the ultrasound image. Further, when an input of the freeze button 272 is sensed while scanning the ultrasound image, the ultrasound diagnosis apparatus 200*b* may maintain a state in which a frame image at a corresponding moment is displayed.

Meanwhile, the button, the track ball, the jog switch and the knob included in the control panel 265 may be provided to the main display unit 221 or the sub-display unit 222 as a GUI.

Referring to FIG. 4C, the ultrasound diagnosis apparatus 200*c* may be implemented as a portable type. Examples of the portable ultrasound diagnosis apparatus 200*c* may include smart phones, laptop computers, PDAs, and tablet PCs including a probe and an application, but are not limited thereto.

The ultrasound diagnosis apparatus 200*c* may include the probe 20 and a main body 240, and the probe 20 may be connected to one side of the main body 240 by a wire or wirelessly. The main body 240 may include a touch screen 245. The touch screen 245 may be configured to display an ultrasound image, various information processed in the ultrasound diagnosis apparatus, and a GUI.

Figure 5A:
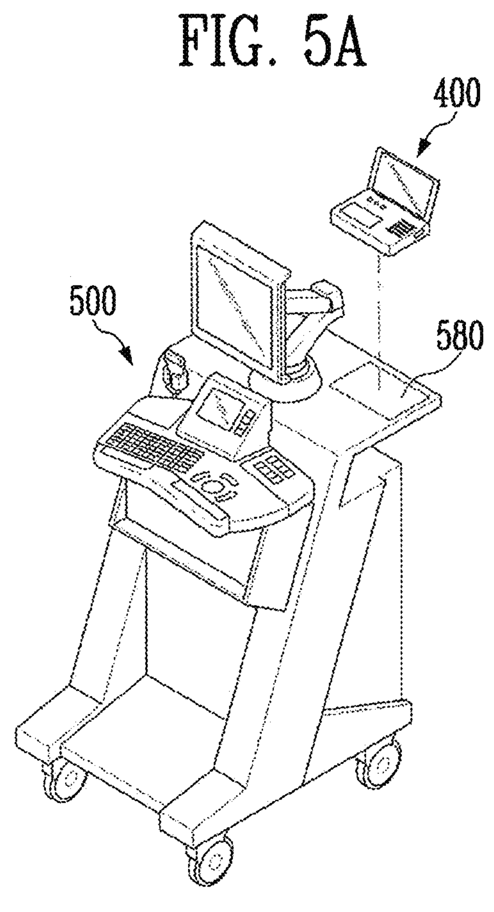
FIGS. 5A to 5C are perspective views of an ultrasound diagnosis apparatus 500 in accordance with at least one embodiment of the present disclosure.
Figure 5B:
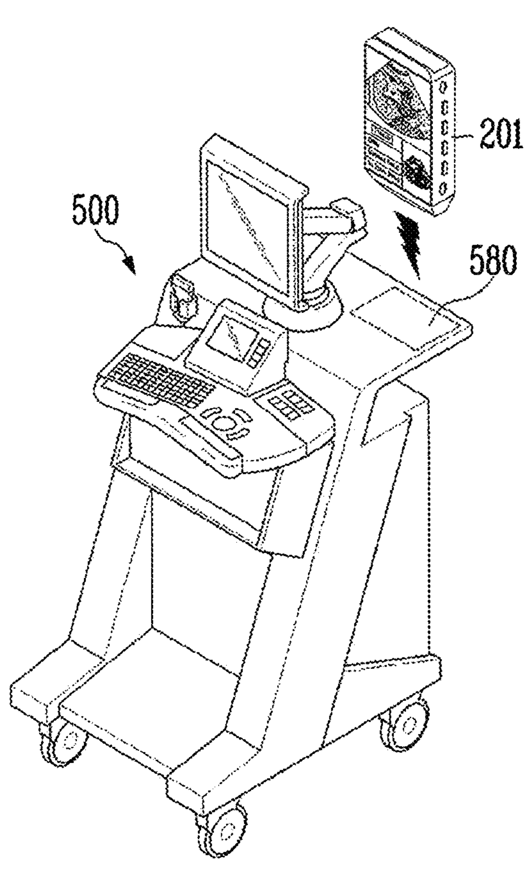
Figure 5C:
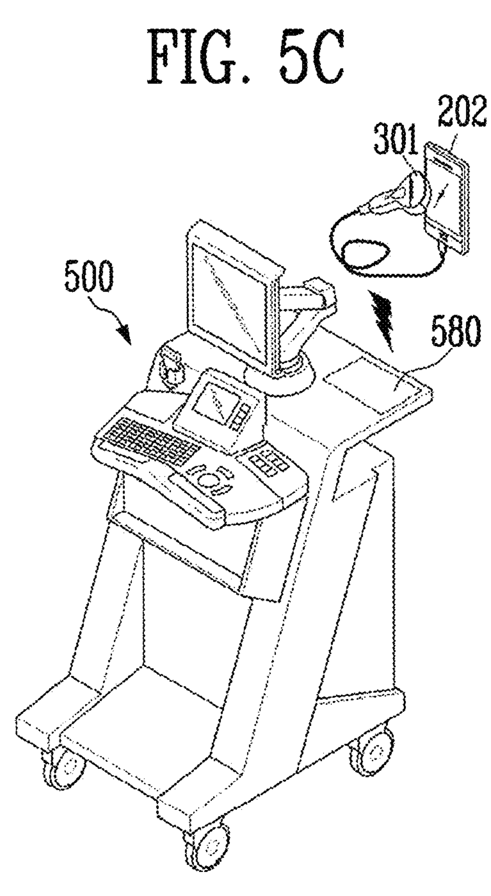

FIGS. 5A to 5C are perspective views of an ultrasound diagnosis apparatus 500 in accordance with at least one embodiment of the present disclosure.

Referring to FIG. 5A, the ultrasound diagnosis apparatus used indoors or an indoor ultrasound diagnosis apparatus 500 generally refers to a non-portable ultrasound diagnosis apparatus used for ultrasound diagnosis, and such an ultrasound diagnosis apparatus 500 is also called cart base equipment. Although the ultrasound diagnosis apparatus 500 is not necessarily used only indoors, it will be referred to as an indoor ultrasound diagnosis apparatus 500 for convenience.

The indoor ultrasound diagnosis apparatus 500 may have a portable docking unit 580 connected to a portable ultrasound diagnosis apparatus 400, and since all components except for the portable docking unit 580 of the indoor ultrasound diagnosis apparatus 500 used in an embodiment of the present disclosure are generally used, a detailed description thereof will be omitted.

Unlike the portable ultrasound diagnosis apparatus 400, the indoor ultrasound diagnosis apparatus 500 has fewer restrictions in terms of size, weight, power consumption, etc., so that diagnosable area is diverse, and it may be developed with high performance. When the portable ultrasound diagnosis apparatus 400 is mounted onto the indoor ultrasound diagnosis apparatus 500, it is possible to use the portable ultrasound diagnosis apparatus 400 with high performance. However, the position at which the portable ultrasound diagnosis apparatus 400 is mounted on the indoor ultrasound diagnosis apparatus 500 may be anywhere with no limitation where it is convenient for the user to use the portable ultrasound diagnosis apparatus 400 and the indoor ultrasound diagnosis apparatus 500 at the same time, and it is not limited by FIG. 5A. Furthermore, the portable ultrasound diagnosis apparatus 400 may be connected to the indoor ultrasound diagnosis apparatus 500 through a wire or integrally.

Referring to FIGS. 5A and 5B, the portable ultrasound diagnosis apparatus 400 in FIG. 5A may correspond to a portable ultrasound diagnosis apparatus 201 in FIG. 58.

It may be integrated with a probe (not shown) including a plurality of transducer elements. Specifically, the portable ultrasound diagnosis apparatus 400 refers to an apparatus that is connected to the indoor ultrasound diagnosis apparatus 500 using a wireless or wired communication method (including Universal Serial Bus (USB)) to provide an ultrasound image to the user using received ultrasound image data. For example, the portable ultrasound diagnosis apparatus 400 may be a smart device in which an application is downloaded and installed in a smart phone.

Specifically, the portable ultrasound diagnosis apparatus 400 may be an apparatus that is connected to the indoor ultrasound diagnosis apparatus 500 through a wired or wireless communication method to provide an ultrasound image to the user using the received ultrasound image data.

For example, the wireless communication method may include at least one of short-range data communication methods including a 60 GHz (mmWave) wireless local area network (WLAN). It may be local area network (Wi-Fi), Bluetooth, ZigBee, Wi-Fi Direct (WFD), Infrared Data Association (IrDA), Bluetooth Low Energy (BLE), Near Field Communication (NFC), Wireless Broadband Internet (Wibro), globally interoperable Shared Wireless Access Protocol (SWAP) for Microwave Access (WiMAX), Wireless Gigabit Alliance (WiGig), and radio frequency (RF).

FIG. 5B illustrates an ultrasound diagnosis system in which the portable ultrasound diagnosis apparatus 201 is connected to a cart-based ultrasound diagnosis apparatus 500.

The cart-based ultrasound diagnosis apparatus 500 may be connected to the portable ultrasound diagnosis apparatus 201 using the aforementioned wireless communication method. Specifically, the portable ultrasound diagnosis apparatus 201 may include at least one wireless communication module (not shown) for performing at least one of the aforementioned wireless communication methods. Furthermore, a portable docking unit 580 in the cart-based ultrasound diagnosis apparatus 500 may include at least one wireless communication module (not shown) for performing wireless communication with the portable ultrasound diagnosis apparatus 201.

In this case, the wireless communication module in the cart-based ultrasound diagnosis apparatus 500 may be a module for performing communication according to at least one of the aforementioned wireless communication methods.

FIG. 5C illustrates an ultrasound diagnosis system in which the portable ultrasound diagnosis apparatus 202 is connected to the cart-based ultrasound diagnosis apparatus 500.

The portable ultrasound diagnosis apparatus 202 may be coupled to the probe 301 through a probe port. The portable ultrasound diagnosis apparatus 202 may be configured to generate an ultrasound image by using the ultrasound image corresponding to the ultrasound signal received by the probe 301 to display the ultrasound image on the display unit.

The cart-based ultrasound diagnosis apparatus 500 may be connected to the portable ultrasound diagnosis apparatus 202 using the aforementioned wireless communication method. The connection through wireless communication between the cart-based ultrasound diagnosis apparatus 500 and the portable ultrasound diagnosis apparatus 202 corresponds to the connection between the cart-based ultrasound diagnosis apparatus 500 and the portable ultrasound diagnosis apparatus 201, and thus a detailed description thereof will be omitted.

Hereinafter, an embodiment of an ultrasound remote diagnosis system applicable to at least one of the ultrasound diagnosis apparatuses described with reference to FIGS. 1 to 3 will be described.

Figure 6A:
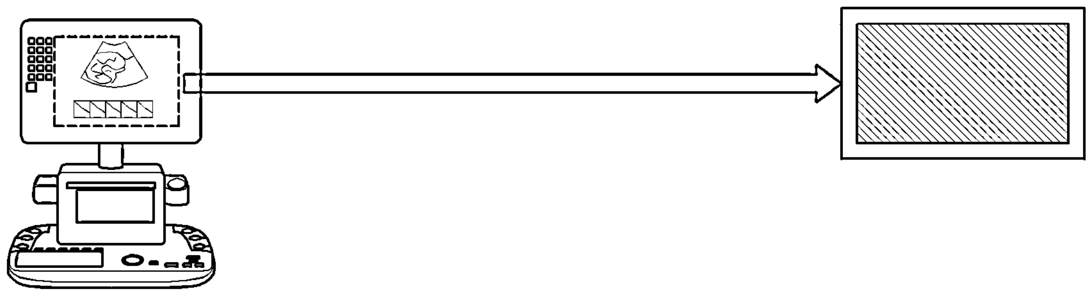
FIG. 6A is a diagram for explaining a conventional ultrasound remote diagnosis system.

FIG. 6A is a diagram for explaining a conventional ultrasound remote diagnosis system.

The conventional ultrasound remote diagnosis system illustrated in FIG. 6A may be configured to transmit only a portion corresponding to the main panel of the ultrasound apparatus main body to a monitor at a remote location, so that only the main panel on which an ultrasound image is displayed may be displayed on the monitor at a remote location. In this case, portions corresponding to the touch panel and the control panel, which are one component of the ultrasound apparatus main body, are not displayed on the remote monitor.

Figure 6B:
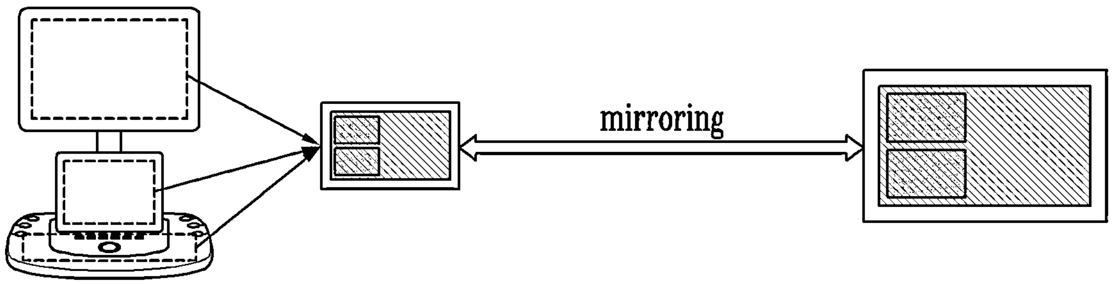
FIG. 6B is a diagram for explaining a conventional ultrasound remote diagnosis system.

FIG. 6B is a diagram for explaining a conventional ultrasound remote diagnosis system.

The conventional ultrasound remote diagnosis system shown in FIG. 6B is a system in which parts corresponding to the main panel, touch panel, and control panel of the ultrasound apparatus are all displayed on a remote monitor, which is a mirroring technology that transmits the main panel, touch panel, and control panel as one signal to the monitor of a remote device.

It is a method in which the entire image displayed on the main body monitor is transmitted at once while the main panel, the touch panel, and the control panel corresponding to the ultrasound image are displayed on the monitor of the ultrasound apparatus main body. In the conventional system of FIG. 6B, while all three screens of the main panel, the touch panel, and the control panel are displayed on the monitor of the remote device, in a state in which the screen corresponding to the main panel is displayed on the entire remote monitor, the screens corresponding to the touch panel and the control panel are displayed in a overlapped form.

It is a technology in which three pieces of information are transmitted as one signal, and since the screen may only be displayed in the form of overlapping screens on the monitor of the remote device, the user cannot see the entire screen corresponding to the main panel, which is inconvenient for diagnosis. This is because, in order to confirm the ultrasound image, the diagnosis must be performed while moving the ultrasound image to a position that does not overlap the screens corresponding to the touch panel and the control panel.

An ultrasound remote diagnosis system 700 and a diagnosis method according to the present disclosure are intended to improve the above inconvenience and will be described below.

Figure 7A:
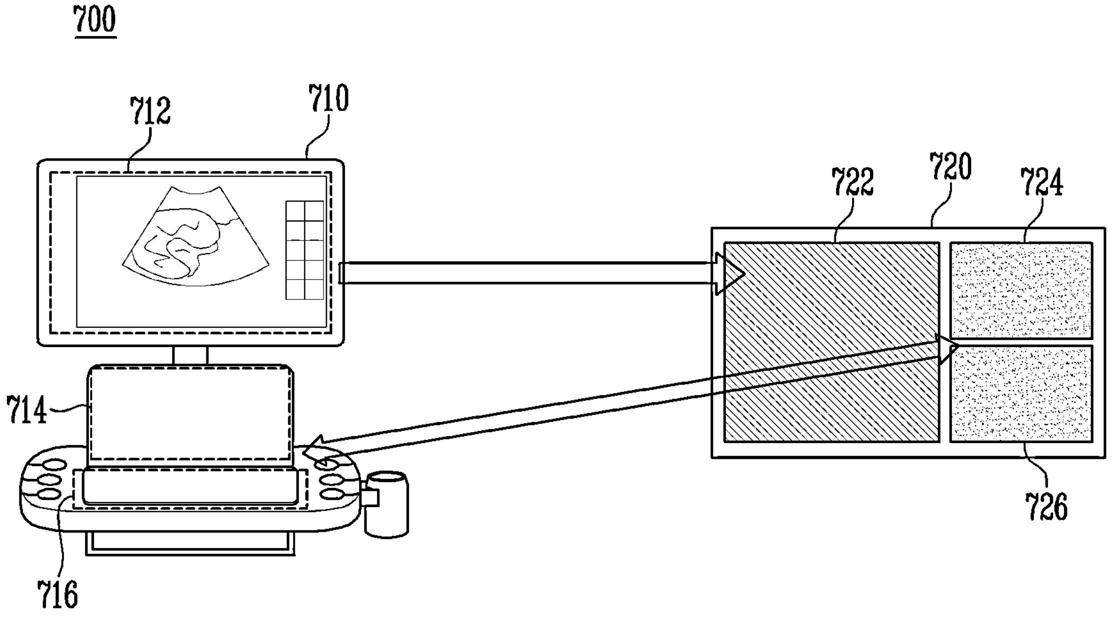
FIG. 7A is a diagram for explaining an ultrasound remote diagnosis system 700 in accordance with an embodiment of the present disclosure.

FIG. 7A is a diagram for explaining the ultrasound remote diagnosis system 700 in accordance with an embodiment of the present disclosure.

As illustrated in FIG. 7A, the ultrasound remote diagnosis system 700 according to an embodiment of the present disclosure includes a main body 710 including a main panel 712, a touch panel 714, and a control panel 716, and a remote device 720 in communication with the main body 710.

The remote device 720 is configured to independently receive, among display data which is real-time image information of the main panel 712, first control data which is real-time image information of the touch panel 714, and second control data which is a virtual control panel corresponding to the control panel 716, at least each information corresponding to the display data and the first control data, from the main body 710, and display a display part 722, a first controller 724, and a second controller 726 respectively corresponding to the display data, the first control data, and the second control data so as not to overlap, and the main body 710 is configured to, in a measurement mode for measuring an object based on a marker set in an ultrasound image displayed on the main panel 712, receive the marker information for measurement input to at least one of the display part 722, the first controller 724, and the second controller 726 of the remote device 720 and display on the main panel 712.

According to another embodiment of the present disclosure, the ultrasound remote diagnosis system 700 includes a remote device 720 in communication with a main body 710 including a main panel 712, a touch panel 714, and a control panel 716.

The remote device 720 independently receives, among display data which is real-time image information of the main panel 712, first control data which is real-time image information of the touch panel 714, and second control data which is a virtual control panel corresponding to the control panel 716, at least each information corresponding to the display data and the first control data, from the main body 710, and display a display part 722, a first controller 724, and a second controller 726 respectively corresponding to the display data, the first control data, and the second control data so as not to overlap, and in a measurement mode for measuring an object based on a marker set in an ultrasound image displayed on the main panel 712, the marker information for measurement input to at least one of the display part 722, the first controller 724, and the second controller 726 is transmitted to the main body 710 to be displayed on the main panel 712.

According to another embodiment of the present disclosure, the ultrasound remote diagnosis system 700 includes a main body 710 in communication with a remote device 720.

In order for the remote device 720 to display a display part 722, a first controller 724, and a second controller 726 respectively corresponding to display data which is real-time image information of the main panel 712, first control data which is real-time image information of the touch panel 714, and second control data which is a virtual control panel corresponding to the control panel 716, so as not to overlap, the main body 710 independently transmits, among the display data, the first control data and the second control data, at least each information corresponding to the display data and the first control data, to the remote device 720, and in a measurement mode for measuring an object based on a marker set in an ultrasound image displayed on the main panel 712, the marker information for measurement input to at least one of the display part 722, the first controller 724, and the second controller 726 is received by the main body 710 to be displayed on the main panel 712.

In FIGS. 6A and 6B described above, while information corresponding to the main panel, touch panel, and control panel of the conventional main body was transmitted to a remote device in the form of a single signal, unlike this, in the ultrasound remote diagnosis system 700 according to the present disclosure, information corresponding to the main panel 712, the touch panel 714, and the control panel 716 of the main body 710 are transmitted to the remote device 720 as separate signals, and accordingly, each of the display part 722, the first controller 724, and the second controller 726 may be displayed on the remote device 720 without overlapping and may be independently controlled.

In the present disclosure, information corresponding to the main panel 712, the touch panel 714, and the control panel 716 of the main body 710 are transmitted to the remote device 720 as separate signals to independently control each of the display part 722, the first controller 724, and the second controller 726 in the remote device 720, and according to another embodiment, after being transmitted so as to overlap, they may be independently resized and displayed so as not to overlap.

The remote device 720 may include a monitor and, depending on the embodiment, may include a virtual monitor type such as AR/VR/MR.

The ultrasound scan screen may be displayed on the display part 722 in real time, and the first controller 724 corresponding to the real-time image of the touch panel 714 may be displayed as a moving picture.

For reference, in the case of the prior art in which the control panel itself is a touch panel, the main panel corresponds to a vertical type. In this case, as described above, the transmission method from the main body to the remote device in the prior art is to transmit the entire screen of the main body as one signal, and the entire screen displayed on the main body has no choice but to be integrated and moved, so the main panel and control panel are transmitted as they are arranged vertically. The monitor of the remote device is generally of a horizontal type, and in this case, it is difficult to display the vertical type arranged on the main body as it is, and even if it is displayed, there was a problem that the screen is small or cut off.

The present disclosure is a technology characterized in that the main panel 712, the touch panel 714, and the control panel 716 of the main body 710 are each independently transmitted as separate signals to the remote device 720, and regardless of whether the main body 710 and the remote device 720 are horizontal or vertical, there is an advantage in that a complete screen may be easily displayed.

The second controller 726 in the present disclosure is a virtual control panel corresponding to the control panel 716 of the main body 710 and may have the same shape as the actual control panel 716 of the main body 710. Specifically, the screen displayed on the second controller 726 is matched to the control panel 716, which is the hardware of the actual main body 710, and the virtual control panel having shapes and functions matching the buttons provided in the control panel 716 and the functions by the buttons may be displayed.

in other words, the same shape as that of the control panel 716 may be displayed on the second controller 726 based on the second control data that is information about the control panel 716 model.

In the remote device 720 of the present disclosure, each screen of the display part 722, the first controller 724, and the second controller 726 is displayed separately, which is convenient for image manipulation or viewing detailed screens.

In the present disclosure, the user may manipulate the first controller 724 and the second controller 726 displayed on the remote device 720 by using the remote mouse 750.

The first controller 724 may be clicked with the remote mouse 750, and at this time, the input value through the remote mouse 750 is changed to relative position information on the screen and transmitted to the main body 710 so that the operation may be performed.

In addition, the second controller 726 may be manipulated by clicking or dragging, or may be manipulated using a mouse wheel.

For example, in the case of a configuration in which the manipulation configuration of the control panel 716 of the main body 710 is a manipulation method of rotating in the + and − directions, as a manipulation method of the second controller 726 displayed on the remote device 720, parts marked with + and − may be clicked with the remote mouse 750 and manipulated. Alternatively, the configuration actually rotated in the control panel 716 may be rotated by a drag method using the remote mouse 750 in the remote device 720, and + and − may be manipulated according to the direction in which the wheel is rolled.

Manipulation buttons and manipulation contents frequently used by the user may be designated in advance to specific keys on the remote keyboard 760, and may be used as shortcut keys.

The measurement mode means measuring an object included in an ultrasound image, and in the measurement mode, an object to be measured may be measured based on a marker displayed on an ultrasound image. The markers will be described with reference to FIGS. 10A to 10D and FIGS. 11A to 11I below.

One or more remote devices 720 capable of remote access to the main body 710 may be provided, and hereinafter, the case where there is one remote device 720 has been described, but when there are a plurality of remote devices 720, the same method may be used.

Figure 7B:
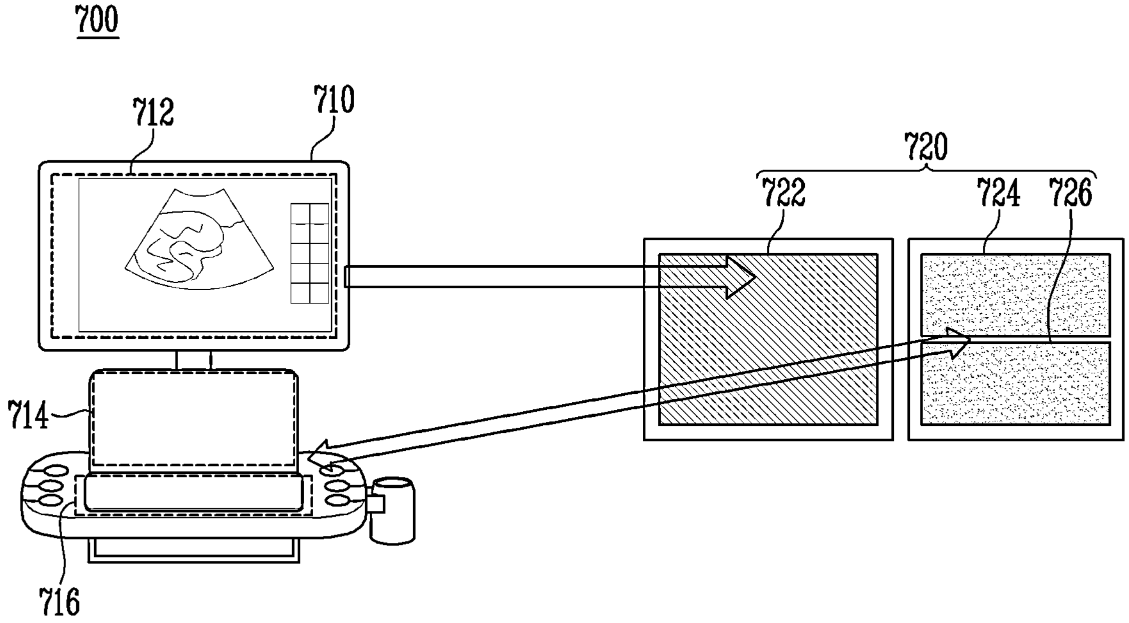
FIG. 7B is a diagram for explaining an ultrasound remote diagnosis system 700 in accordance with another embodiment of the present disclosure.

FIG. 7B is a diagram for explaining an ultrasound remote diagnosis system 700 in accordance with another embodiment of the present disclosure.

FIG. 7B illustrates a case where the monitor of the remote device 720 is a dual monitor consisting of a first monitor and a second monitor, and in this case, the display part 722 may be displayed on the first monitor, and the first controller 724 and the second controller 726 may be displayed on the second monitor.

The monitor of the remote device 720 according to the present disclosure may be of a horizontal type having a longer horizontal length compared to vertical as shown in FIGS. 7A and 7B, but may also be of a vertical type having a long vertical length.

In the case of a vertical monitor, the display part 722 may be displayed on the upper side of the monitor of the remote device 720, and the first controller 724 and the second controller 726 may be displayed on the lower side of the monitor of the remote device 720, and conversely, the display part 722 may be disposed on the lower side, and the first controller 724 and the second controller 726 may be disposed on the upper side for display.

The position of each screen displayed on the monitor of the remote device 720 is not limited to the above-described positions, and may include all cases where the screen is displayed without overlapping portions on the screen.

Figure 8:
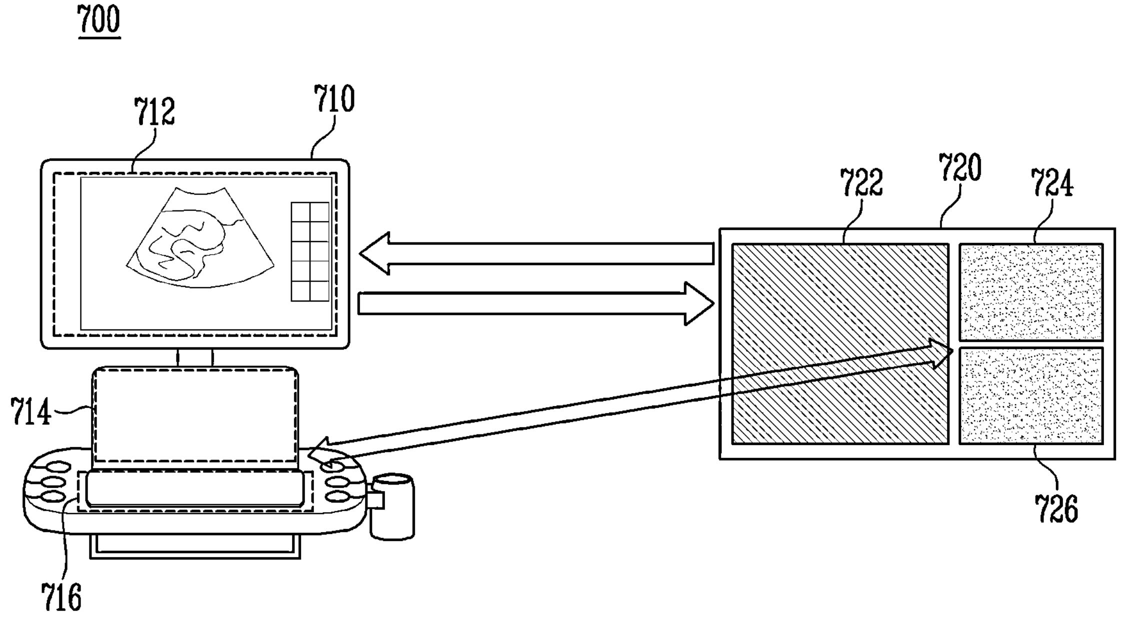
FIG. 8 is a diagram for explaining a measurement mode of the ultrasound remote diagnosis system 700 in accordance with an embodiment of the present disclosure.

FIG. 8 is a diagram for explaining a measurement mode of the ultrasound remote diagnosis system 700 in accordance with an embodiment of the present disclosure.

As shown in FIG. 8, in the ultrasound remote diagnosis system 700 according to an embodiment of the present disclosure, in the measurement mode, information input to the display part 722 may be transmitted to the main body 710 and may be displayed on the main panel 712.

In the present disclosure, the touch panel 714 and the first controller 724, the control panel 716 and the second controller 726 may each independently perform two-way transmission and reception. However, in case of non-measurement mode, between the main panel 712 of the main body 710 and the display part 722 of the remote device 720, only one-way information transmission is possible from the main panel 712 of the main body 710 to the display part 722 of the remote device 720.

On the other hand, in the measurement mode, as shown in FIG. 8, the main panel 712 of the main body 710 and the display part 722 of the remote device 720 may transmit and receive information in both directions.

The ultrasound remote diagnosis system 700 according to the present disclosure can execute the measurement mode by controlling the main panel 712 of the main body 710 or by touching the touch panel 714, and in addition, it is possible to execute the measurement mode through the remote device 720. Execution of the measurement mode through the remote device 720 will be described with reference to FIGS. 9A to 9C below.

In the measurement mode, the measurement process performed through the main body 710 and the remote device 720 may be displayed equally on the main panel 712 of the main body 710 and the display part 722 of the remote device 720.

When the ultrasound remote diagnosis system 700 of the present disclosure enters the measurement mode, a first pointer (not shown) corresponding to the mouse cursor of the main body 710 may be displayed on the display part 722, a second pointer 740 corresponding to the mouse cursor of the remote device 720 may be displayed, or both the first pointer (not shown) and the second pointer 740 may be displayed.

When there are a plurality of remote devices 720, each remote device 720 may independently execute a measurement mode.

In this case, the measuring process may be displayed not only on the remote device 720 that performs the measurement, but also on other remote devices 720. When measurement is performed simultaneously in a plurality of remote devices 720, a display method and a display order are not limited herein.

Figure 9A:
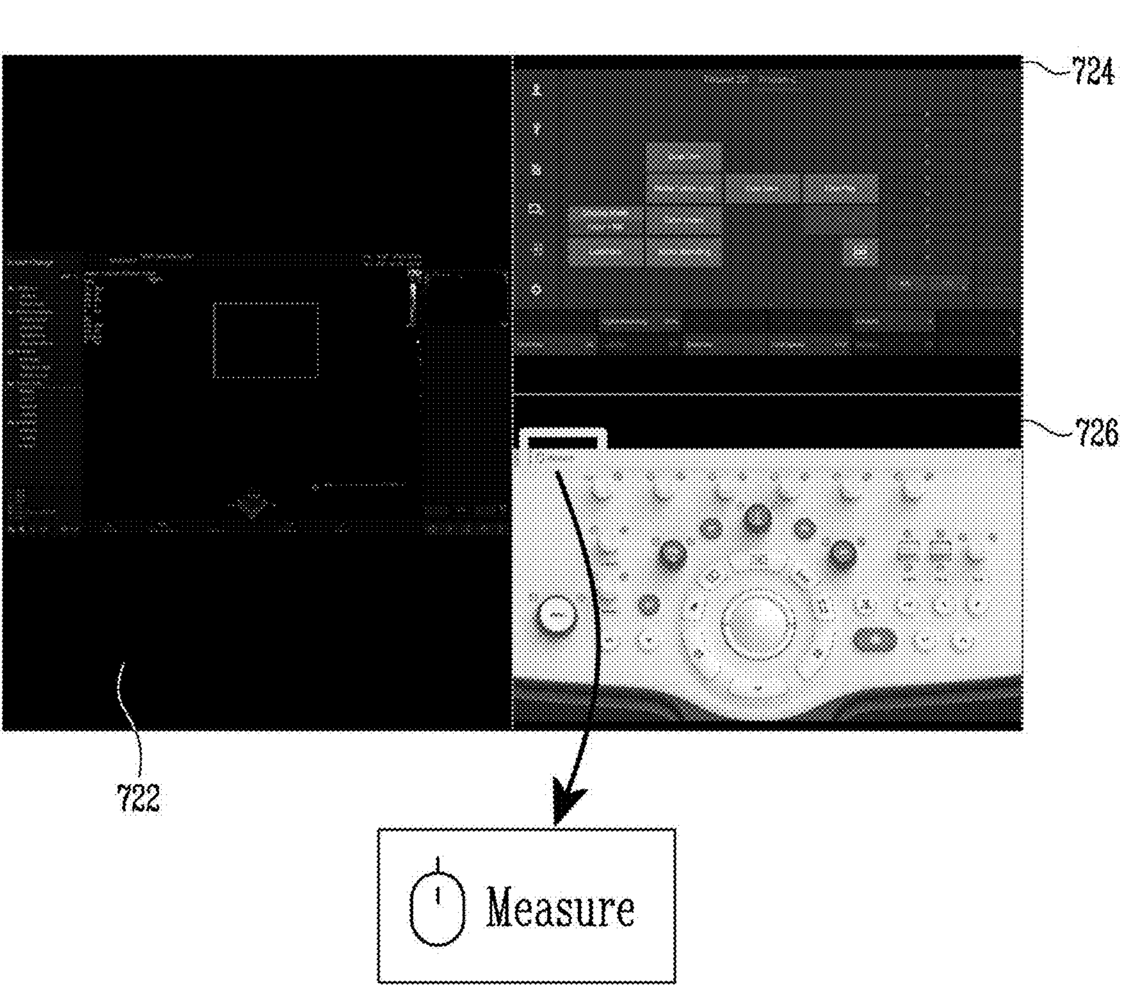
FIG. 9A is a diagram for explaining a process of executing the measurement mode of the ultrasound remote diagnosis system 700 in accordance with an embodiment of the present disclosure.

FIG. 9A is a diagram for explaining a process of executing a measurement mode of the ultrasound remote diagnosis system 700 in accordance with an embodiment of the present disclosure.

In the ultrasound remote diagnosis system 700 of the present disclosure, in order to execute the measurement mode, the measurement mode must first be started, and the starting of the measurement mode may be the same as the method of starting the measurement mode in the existing ultrasound apparatus.

In the present disclosure, before the user executes the measurement mode, the user must enter the measurement mode, so in a state in which the measurement mode is entered, measurement may be performed through the same operation as in the description of FIGS. 9A to 9C below.

In the ultrasound remote diagnosis system 700 according to an embodiment of the present disclosure, a distance to be measured, a line trace, a circumference, a thickness, an area, a volume, etc., of an object to be measured may be measured through the measurement modes for the various modes described above.

The types of measurement modes are not limited to those listed above and may include all of various measurement modes utilized in the ultrasound apparatus.

Execution of the measurement mode in the present disclosure may be performed through the control of the second controller 726, and as an embodiment, as shown in FIG. 9A, it may be executed by pressing the 'measurement' button located on the second controller 726.

As another embodiment, the measurement mode may be executed only by moving the second pointer 740, which will be described with reference to FIGS. 9B and 9C.

Figures 9B, 9C:
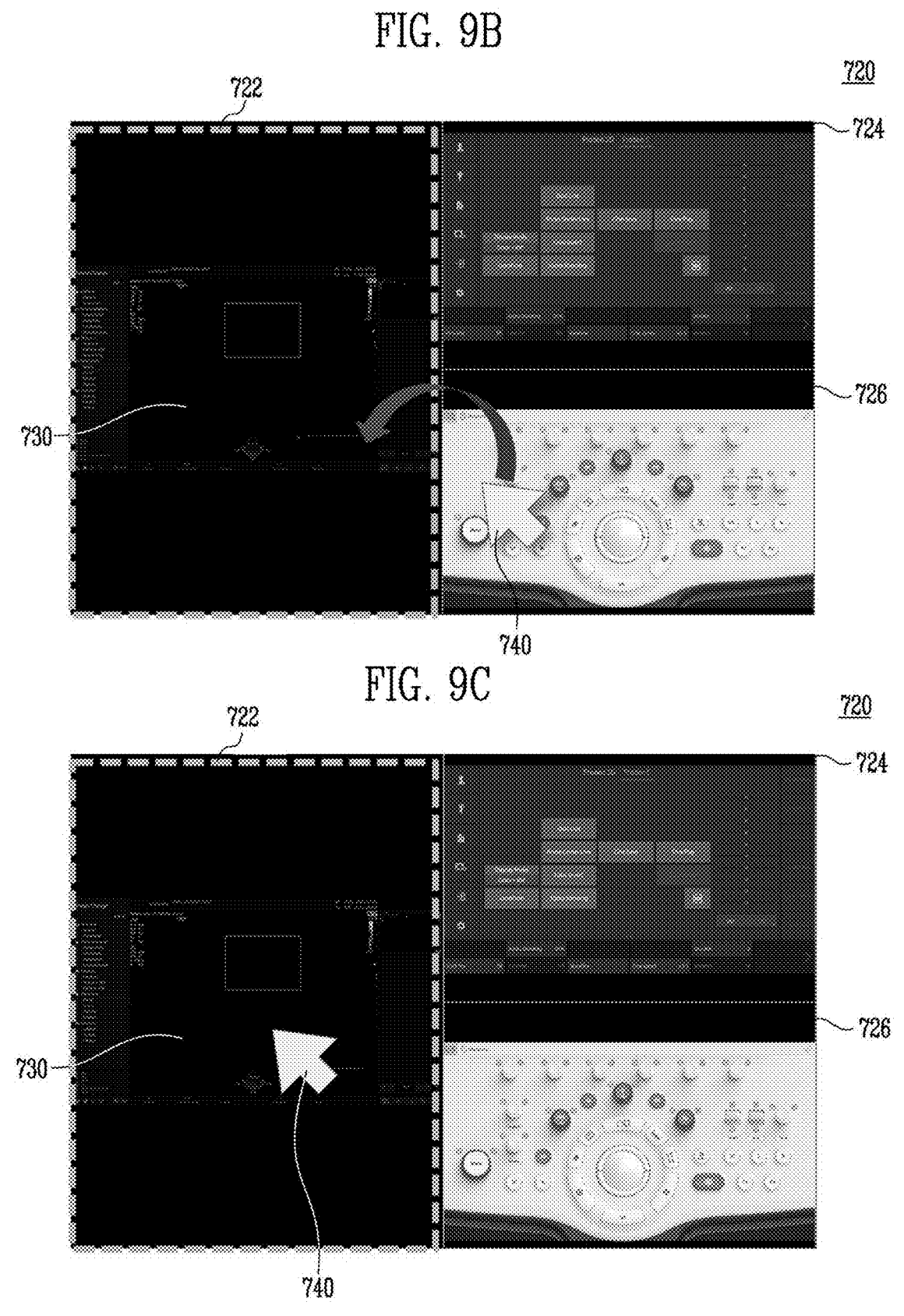

FIGS. 9B and 9C are a diagram for explaining a process of executing a measurement mode of the ultrasound remote diagnosis system 700 in accordance with an embodiment of the present disclosure.

FIG. 9B is a state in which the second pointer 740 is located in the area of the second controller 726, and FIG. 9C is a state in which the second pointer 740 is moved to the display part 722.

As shown in FIG. 9C, the measurement mode may be executed by moving the second pointer 740 inside an area of the display part 722, i.e., inside the image area 730 where an image is displayed.

In the measurement mode, since the main panel 712 of the main body 710 and the display part 722 of the remote device 720 may transmit and receive information in both directions, measurement in the measurement mode may use at least one of a first pointer (not shown) and a second pointer 740.

Since the measurement method using a first pointer (not shown) corresponding to the mouse cursor of the main body 710 is similar to the measurement method in a general ultrasound apparatus, hereinafter, a measurement method using the second pointer 740 corresponding to the mouse cursor of the remote device 720 will be described.

FIGS. 10A to 10D are a diagram for explaining a remote measurement process in the ultrasound remote diagnosis system 700 in accordance with an embodiment of the present disclosure.

First, as shown in FIGS. 10A to 10D, when the second pointer 740 corresponding to the mouse cursor of the remote device 720 is located within the area of the display part 722, the second pointer 740 may be expressed in the form of measurement markers 742 and 744.

A first measurement marker 742 is displayed at the point where the second pointer 740 is located, a first point 743 is specified by clicking the first measurement marker 742, and when the second pointer 740 moves, a second measurement marker 744 is displayed at the moved location, and the second point 745 may be specified by clicking the second measurement marker 744.

In the present disclosure, the second pointer 740 may be moved by manipulating the remote mouse 750, and the remote trackball 727 of the second controller 726, which is a virtual control panel, may be easily manipulated by manipulating the remote mouse 750.

Looking at the measurement process through FIGS. 10A to 10D, FIG. 10A is a view in which the second pointer 740 is moved to the starting location for measuring the object in order to measure the object located in the display part 722, which is a state where the first measurement marker 742 is displayed at the point where the second pointer 740 is located. As the location of the second pointer 740 is moved, the first measurement marker 742 is moved to coincide with the second pointer 740.

Figures 10A, 10B, 10C, 10D:
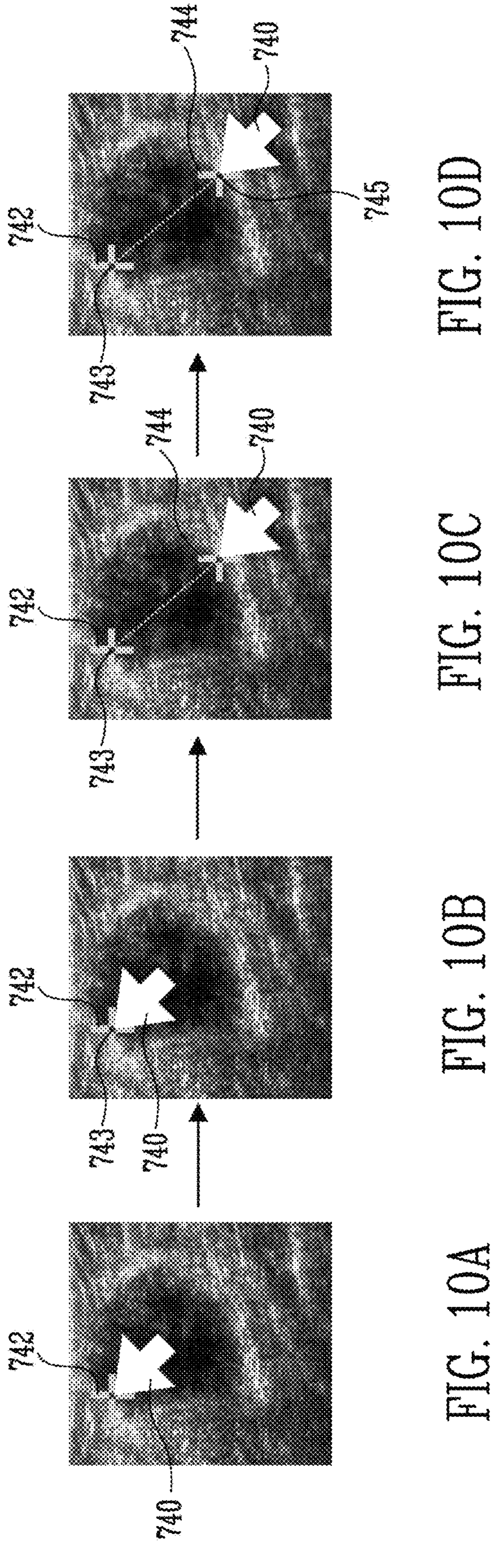
FIGS. 10A to 10D are a diagram for explaining a remote measurement process in the ultrasound remote diagnosis system 700 in accordance with an embodiment of the present disclosure.
Figure 11A:
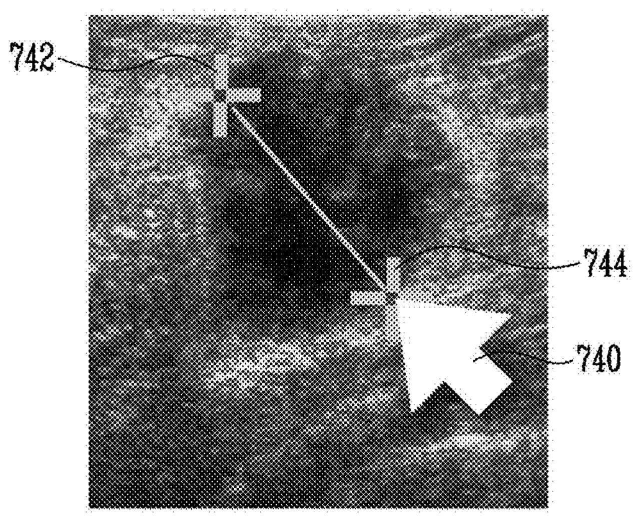
FIGS. 11A to 11I are a diagram illustrating various embodiments of measurement markers 742, 744 and a second pointer 740 in the ultrasound remote diagnosis system 700 in accordance with an embodiment of the present disclosure.
Figure 11B:
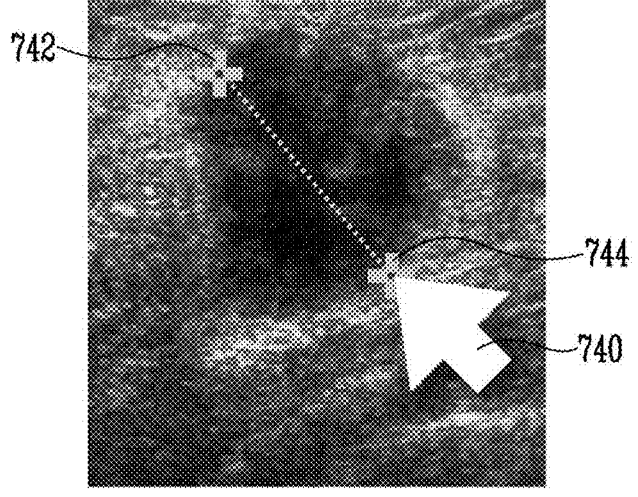
Figure 11C:
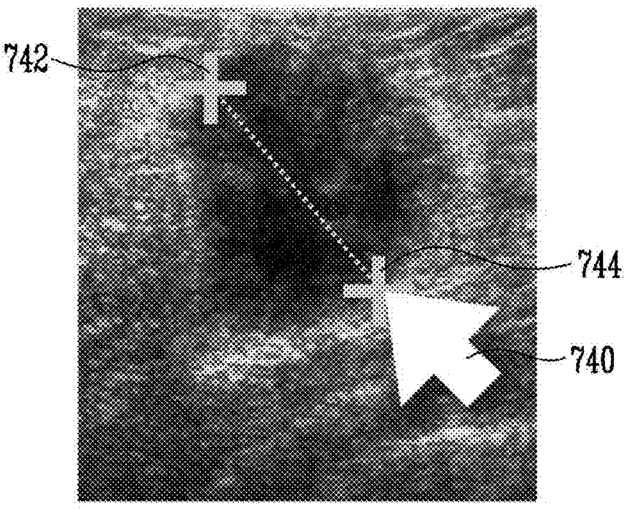
Figure 11D:
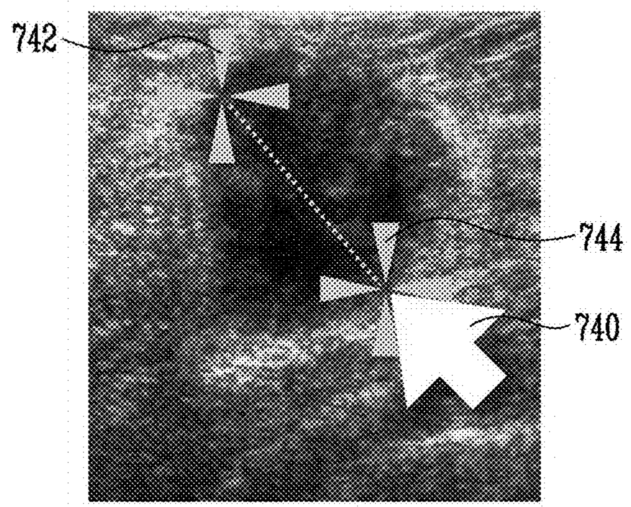
Figure 11E:
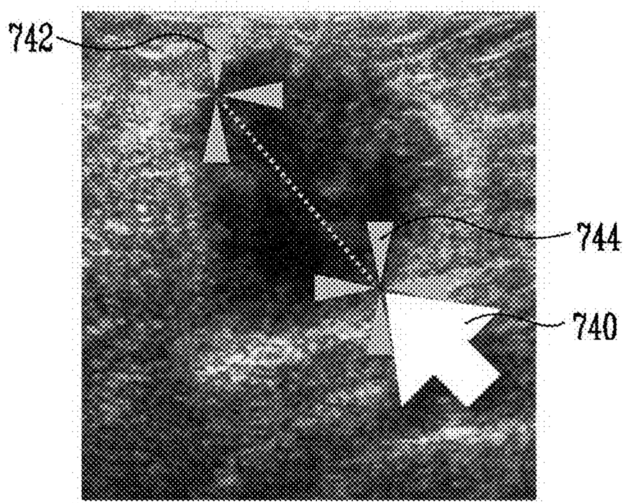
Figure 11F:
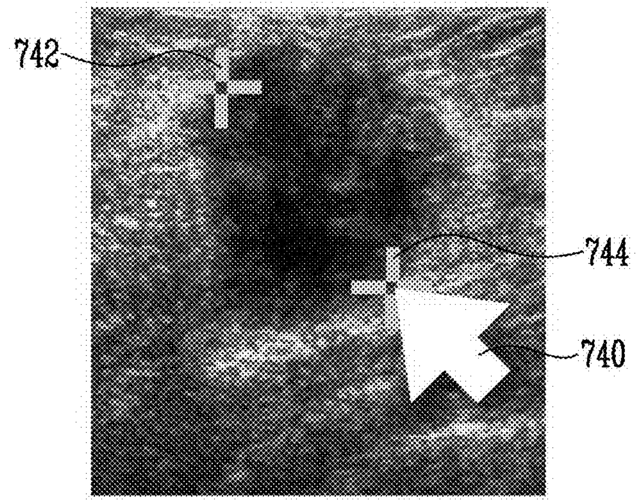
Figure 11G:
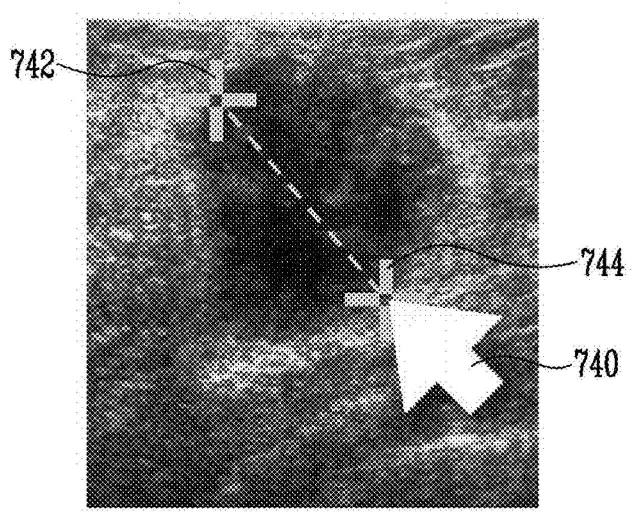
Figure 11H:
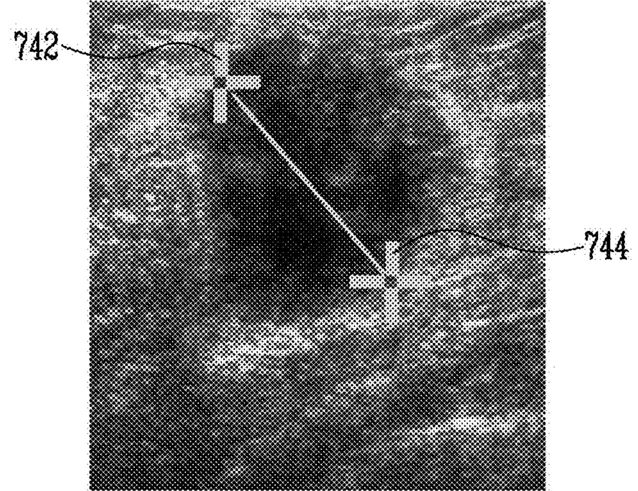
Figure 11I:
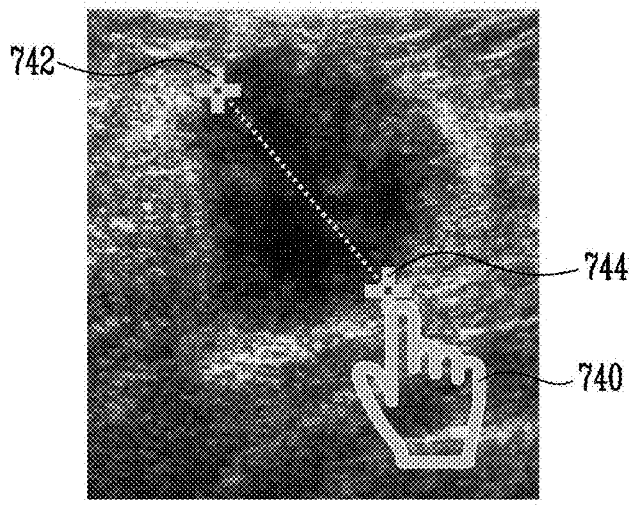

FIG. 10B illustrates a view in which the second pointer 740 is located at a specific location of an object to be measured, i.e., a starting location for measurement, and clicked, and accordingly, the point indicated by the first measurement marker 742 and the starting location for measurement may be specified as the first point 743.

FIG. 10C illustrates that the second pointer 740 is moved to the end location for measuring the object after specifying the first point 743, which is a view in which the second measurement marker 744 is displayed on the moved second pointer 740. While the second pointer 740 is moved by the user, the second measurement marker 744 may be continuously displayed on the second pointer 740 together.

In the present disclosure, in the process of measuring the object through the remote device 720, there is an advantage in that the user may specify the first point 743 and the second point 745 while watching the location of each of the measurement markers 742 and 744 move.

FIG. 10D illustrates a state in which the second pointer 740 is clicked while the second pointer 740 is located at the end location for measurement, and the point indicated by the second measurement marker 744 may be specified as a second point 745.

According to an embodiment, a connection line connecting the first point 743 and the second point 745 may be displayed, and the connection line is displayed on the screen, thereby having the effect of accurate measurement.

In the measurement mode according to the present disclosure, when the second pointer 740 moves, the user may see the first measurement marker 742 and the second measurement marker 744 displayed while moving together, and since it is possible to specify while seeing and determining the location to be measured, it is easy to measure compared to the existing one.

In addition, in the present disclosure, when the second pointer 740 is located on the image area 730 of the display part 722, measurement markers 742 and 744 appear, and when specifying a measurement point, there is no need to move the second pointer 740 again to press a separate button, and the point to be measured is specified simply by placing the second pointer 740 on the point to be specified and clicking, so which is easier than the existing measurement method.

In other words, in the present disclosure, for specifying a point, after locating the second pointer 740 at the first point 743 and the second point 745, when the remote mouse 750 is clicked as it is, the process may be the same as clicking the SET/EXIT button located in the second controller 726 of the remote device 720 corresponding to the control panel 716 of the main body 710.

In contrast, in the existing measurement method, the measurement marker does not appear immediately on the mouse cursor even when the mouse cursor is placed on the image area, but the measurement marker appeared on the mouse cursor only when there is a separate action of clicking the mouse cursor.

In particular, in the process of moving the mouse cursor to the object, since it was possible to move the pointer through mouse drag only within the trackball area on the virtual control panel displayed on the remote monitor, when the object to be measured is larger than the diameter of the trackball, there was inconvenience of moving the measurement marker by dragging the mouse several times. In addition, by moving the mouse pointer in the trackball according to the above description, after locating the measurement marker on the object, in order to specify the first point and the second point, the SET button displayed on the remote monitor screen corresponding to the control panel of the main body should have been clicked, respectively, so the existing method is an indirect measurement method rather than a direct measurement on the image of the object, which causes inconvenience.

FIGS. 11A to 11I are a diagram illustrating various embodiments of measurement markers 742, 744 and a second pointer 740 in an ultrasound remote diagnosis system 700 in accordance with an embodiment of the present disclosure.

As illustrated in FIGS. 11A to 11I, size, shape, and the like of the second pointer 740, the measurement markers 742 and 744, and the connection line connecting the first point 743 and the second point 745 may vary.

The ultrasound remote diagnosis method according to an embodiment of the present disclosure is an ultrasound remote diagnosis method of an ultrasound remote diagnosis system including a main body 710 including a main panel 712, a touch panel 714, and a control panel 716, and a remote device 720 in communication with the main body 710.

The method includes independently receiving, by the remote device 720, among display data which is real-time image information of the main panel 712, first control data which is real-time image information of the touch panel 714, and second control data which is a virtual control panel corresponding to the control panel, at least each information corresponding to the display data and the first control data, from the main body 710, displaying, by the remote device 720, a display part 722, a first controller 724, and a second controller 726 respectively corresponding to the display data, the first control data, and the second control data so as not to overlap, and in a measurement mode for measuring an object based on a marker set in an ultrasound image displayed on the main panel 712, receiving, by the main body 710, the marker information for measurement input to at least one of the display part 722, the first controller 724, and the second controller 726 to display on the main panel 712.

Executing the measurement mode by moving the second pointer 740 inside the area of the display part 722 or by controlling the second control unit 726 may be further included.

In the measurement mode, at least one of a first pointer (not shown) corresponding to a mouse cursor of the main body 710 and a second pointer 740 corresponding to a mouse cursor of the remote device 720 may be displayed on the display part 722, and displaying measurement markers 742 and 744 on the second pointer 740 when the second pointer 740 is located within the object area may be included.

In the measurement mode, specifying the first point 743 by clicking the first measurement marker 742 displayed at the point where the second pointer 740 is located, and specifying the second point 745 by clicking the second measurement marker 744 displayed at the location where the second pointer 740 moves may be included.

Depending on embodiments, displaying a connection line connecting the first point 743 and the second point 745 may be included.

According to an embodiment, the ultrasound diagnosis apparatus according to the present disclosure may be applied not only to an ultrasound apparatus, but also to a diagnostic field performed together with a medical imaging device such as a magnetic resonance imaging (MRI) device, a computed tomography (CT) device, or an X-ray imaging device.

Since detailed information related to each step has been sufficiently described in relation to the ultrasound remote diagnosis system 700 according to an embodiment of the present disclosure, a detailed description thereof will be omitted.

The remote measurement method of the ultrasound remote diagnosis system 700 according to an embodiment of the present disclosure has been described above, and hereinafter, a remote display method of the ultrasound remote diagnosis system 700 according to an embodiment of the present disclosure will be described.

In the case of the conventional ultrasound remote diagnosis, when the control panel of the main body is manipulated, the manipulation process for which manipulation is in progress is not displayed on the monitor of the remote device, but only the result of the manipulation was shown. Therefore, the control panel manipulation process in the main body could not be known at the remote location, so the diagnosis process had to be guessed only through the image of the manipulation result during the ultrasound diagnosis process. In this regard, there were some difficulties in the process of remotely learning to manipulate the ultrasound diagnosis system.

The present disclosure is to improve the difficulty of the existing ultrasound remote diagnosis method as described above, and is characterized in that the manipulation process of the control panel 716 of the main body 710 is displayed on the remote device 720.

At the same time, in the present disclosure, the manipulation process of the second controller 726 of the remote device 720 may be displayed on the control panel 716 of the main body 710, which is significant that when there are a plurality of second controllers 726, the manipulation process of each second controller 726 may be checked from the main body 710.

Figure 12A:
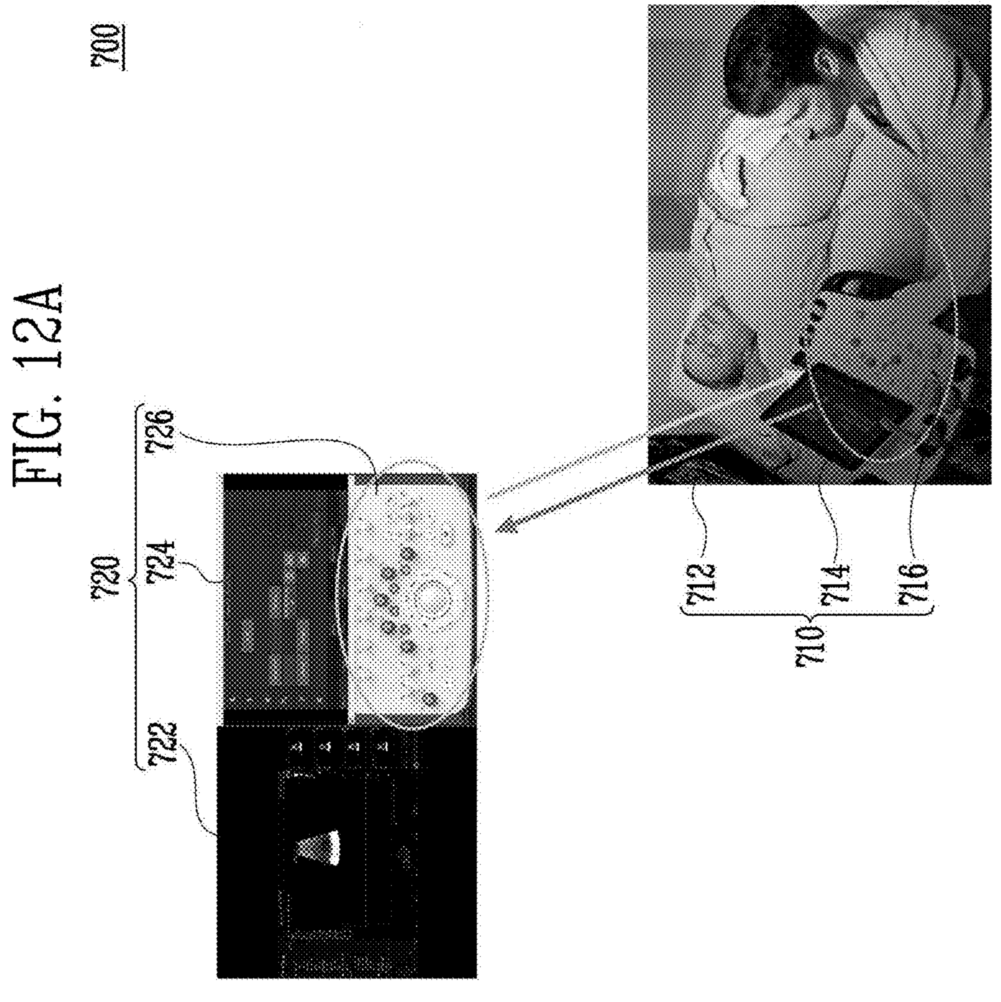
FIG. 12A is a diagram for explaining a display method of the ultrasound remote diagnosis system 700 in accordance with an embodiment of the present disclosure.
Figure 12B:
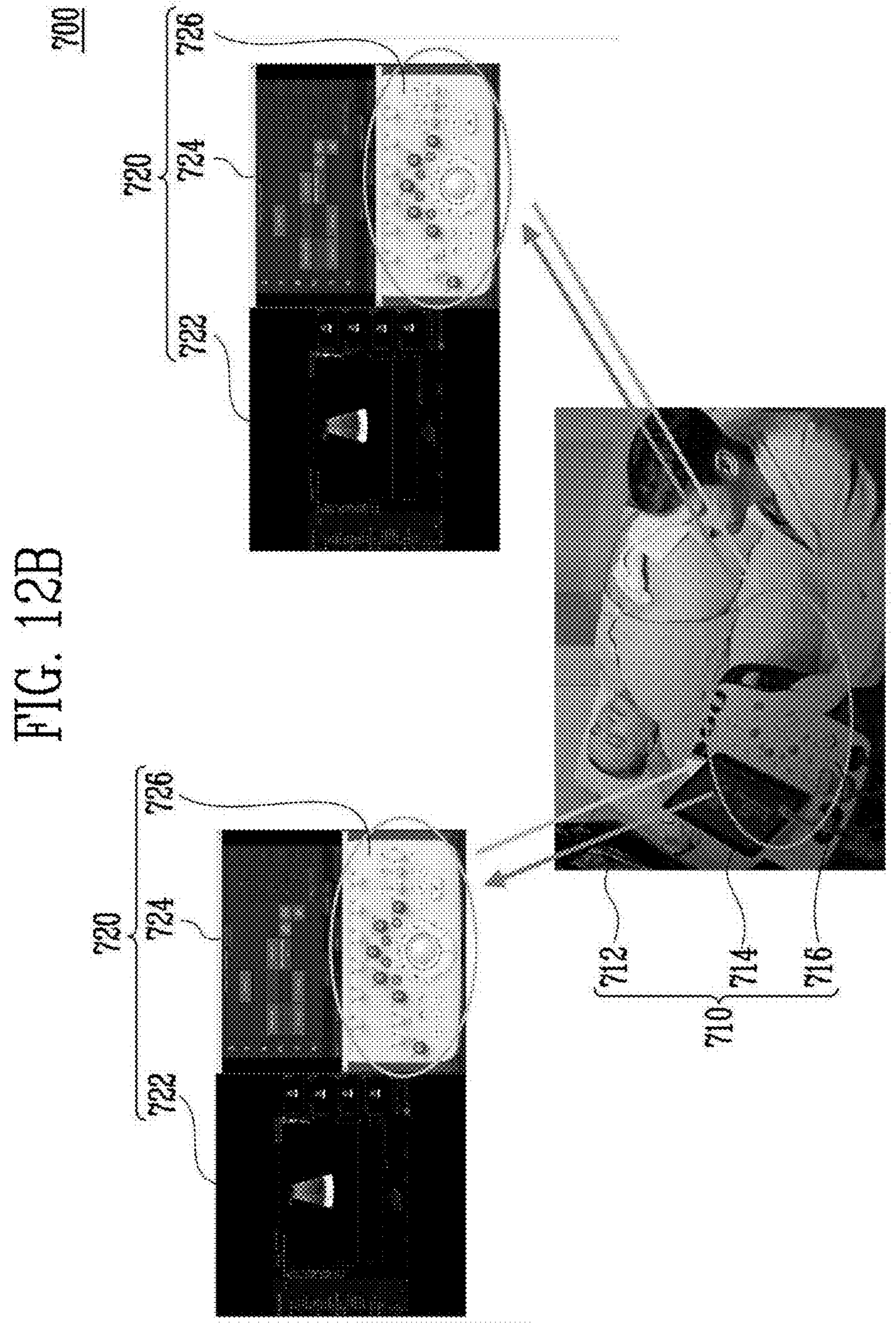
FIG. 12B is a diagram for explaining a display method of the ultrasound remote diagnosis system 700 in accordance with another embodiment of the present disclosure.

FIG. 12A is a diagram for explaining a display method of the ultrasound remote diagnosis system 700 in accordance with an embodiment of the present disclosure, and FIG. 12B is a diagram for explaining a display method of the ultrasound remote diagnosis system 700 in accordance with another embodiment of the present disclosure.

As illustrated in FIGS. 12A and 12B, an ultrasound remote diagnosis system 700 according to an embodiment of the present disclosure includes a main body 710 including a main panel 712, a touch panel 714, and a control panel 716, and a remote device 720 in communication with the main body 710, wherein the remote device 720 is configured to independently receive, among display data which is real-time image information of the main panel 712, first control data which is real-time image information of the touch panel 714, and second control data which is a virtual control panel corresponding to the control panel 716, at least each information corresponding to the display data and the first control data, from the main body 710, and display a display part 722, a first controller 724, and a second controller 726 respectively corresponding to the display data, the first control data, and the second control data so as not to overlap, and in order for manipulation information by any one of the control panel 716 and the second controller 726 to be displayed on the other one, the manipulation information is transmitted mutually between the main body 710 and the remote device 720.

According to another embodiment of the present disclosure, an ultrasound remote diagnosis system 700 includes a remote device 720 in communication with a main body 710 including a main panel 712, a touch panel 714, and a control panel 716, wherein the remote device 720 is configured to independently receive, among display data which is real-time image information of the main panel 712, first control data which is real-time image information of the touch panel 714, and second control data which is a virtual control panel corresponding to the control panel 716, at least each information corresponding to the display data and the first control data, from the main body 710, and display a display part 722, a first controller 724, and a second controller 726 respectively corresponding to the display data, the first control data, and the second control data so as not to overlap, and in order for manipulation information by any one of the control panel 716 and the second controller 726 to be displayed on the other one, the manipulation information is transmitted mutually between the main body 710 and the remote device 720.

According to another embodiment of the present disclosure, an ultrasound remote diagnosis system 700 includes a main body 710 in communication with a remote device 720, wherein the main body 710 includes a main panel 712, a touch panel 714, and a control panel 716, and a remote device 720, in order for the remote device 720 to display a display part 722, a first controller 724, and a second controller 726 respectively corresponding to display data which is real-time image information of the main panel 712, first control data which is real-time image information of the touch panel 714, and second control data which is a virtual control panel corresponding to the control panel 716, so as not to overlap, the main body 710 independently transmits, among the display data, the first control data and the second control data, at least each information corresponding to the display data and the first control data, to the remote device 720, and in order for manipulation information by any one of the control panel 716 and the second controller 726 to be displayed on the other one, the manipulation information is transmitted mutually between the main body 710 and the remote device 720.

In the present disclosure, manipulation information by the control panel 716 may be displayed on the second controller 726 in real time, and the manipulation information by the second controller 726 may be displayed on the control panel 716 in real time.

As illustrated in FIG. 12A, there may be one remote device 720 capable of remote access with the main body 710, and as illustrated in FIG. 12B, a remote device 720 capable of remote access with the main body 710 may be one or more.

A case in which there are a plurality of remote devices 720 will be described in detail with reference to FIGS. 14 and 16 below.

Figure 13:
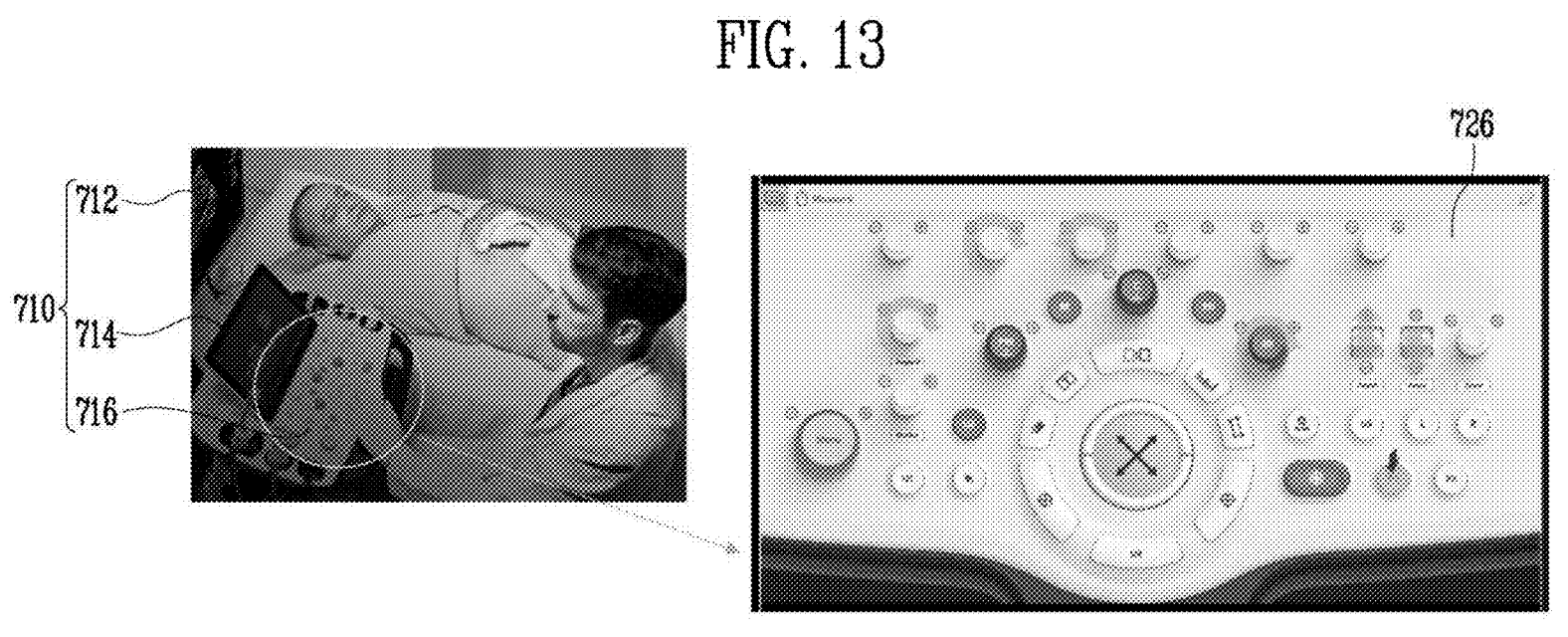

FIG. 13 is a diagram for explaining a display method of the ultrasound remote diagnosis system 700 in accordance with an embodiment of the present disclosure.

As illustrated in FIG. 13, manipulation information by the control panel 716 displayed on the second controller 726 may be displayed as a GUI.

The second controller 726 is a virtual control panel corresponding to the control panel 716 of the main body 710 and may have the same shape as the actual control panel 716 of the main body 710.

In the present disclosure, as the control panel 716 of the main body 710 is manipulated, the manipulation process may be displayed on the second controller 726 in real time so as to match the configuration of the control panel 716 to be manipulated.

Specifically, as illustrated in FIG. 13, around the configuration of the second controller 726 corresponding to the configuration manipulated on the control panel 716, the movement of the corresponding configuration due to the user's manipulation may be displayed in the GUI. As an example, what is displayed in the GUI may be an arrow indicating left and right rotation, vertical movement, a pressed form, and the like.

Figure 14:
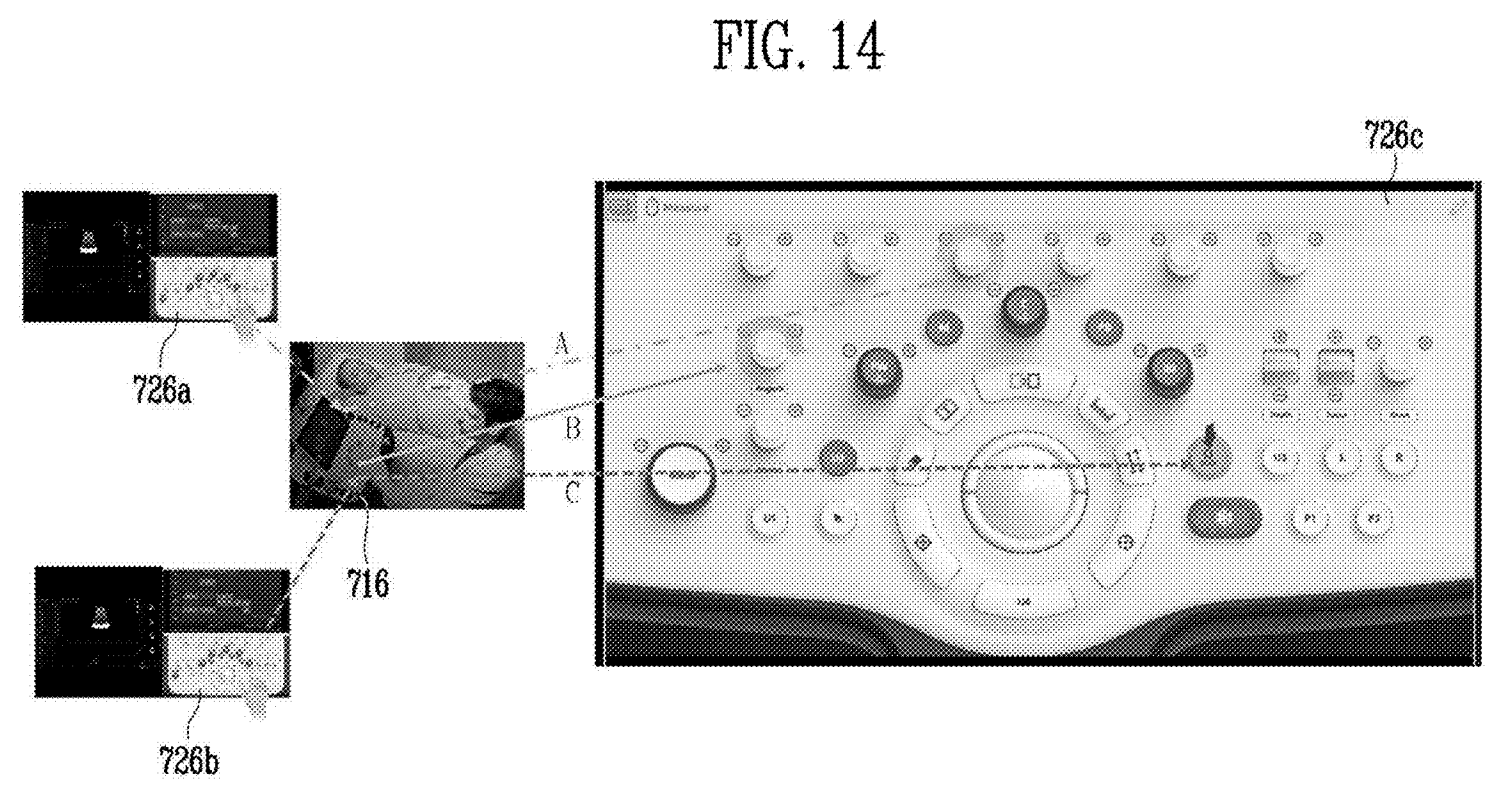

FIG. 14 is a diagram for explaining a display method of the ultrasound remote diagnosis system 700 in accordance with an embodiment of the present disclosure.

FIG. 14 is a diagram illustrating a case where there are a plurality of remote devices 720 capable of remote access to the main body 710, which is a diagram illustrating the plurality of second controllers 726 of the plurality of remote devices 720 as second controllers 726*a*, 726*b*, and 726*c*, respectively.

An example of manipulation through the second controllers 726*a* and 726*b* and the control panel 716 is illustrated. The second controllers 726*a* and 726*b* manipulate as indicated in A and C, respectively, and the control panel 716 manipulate as indicated in B, and the above manipulation process is displayed as a GUI on the second controller 726*c*.

From what is illustrated in FIG. 14, it may be seen that in the second controller 726*a*, a manipulation A of rotating one component at the upper side in a counterclockwise direction was performed, the second controller 726*b* performed a manipulation C of pressing the SCAN button, and an manipulation B of rotating the ANGLE component clockwise in the control panel 716 was performed.

The manipulation information from the second controllers 726*a* and 726*b* is transmitted to the control panel 716 of the main body 710, and an image reflecting a plurality of pieces of manipulation information is displayed on the main body 710, and a real-time image reflecting the manipulation information is equally displayed on each remote device 720.

The manipulation information displayed on the second controller 726*c* may include not only manipulation information by the control panel 716 but also manipulation information via other second controllers 726*a* and 726*b*.

Manipulation information of the plurality of second controllers 726 may be displayed between the plurality of second controllers 726, respectively, and although only the screen of the second controller 726*c* is shown enlarged in FIG. 14, manipulation information of the plurality of second controllers 726 and manipulation information by the control panel 716 may be displayed on the second controller 726*a* and 726*b* as well.

In this case, the plurality of pieces of manipulation information displayed on the second controller 726 may be displayed in mutually distinguished forms.

For example, it may be displayed in a different display format, such as a color, a shape, a line type, and a line thickness displayed in the GUI. Due to the display in the mutually distinguished forms, the user using the remote device 720 may check whether the current manipulation is performed on the main body 710 or, if there are a plurality of remote devices 720, which remote device 720 the manipulation is performed on.

When the manipulation is performed by the plurality of second controllers 726, among the plurality of pieces manipulation information, it may be sequentially displayed starting from the first performed manipulation, and after all of the previously performed manipulation tasks are finished, manipulation information from the other second controller 726 may be displayed.

Alternatively, the manipulation information of the other second controller 726 may be displayed together even before the previously performed manipulation task is finished. In this case, in order to distinguish the manipulation information performed by each second controller 726 and to distinguish the order in which the manipulation is performed, it is possible to display a plurality of pieces of manipulation information so as to be distinguishable, such as numbering the display according to a predetermined criterion or making the displayed color to be gradually darker.

Figure 15:
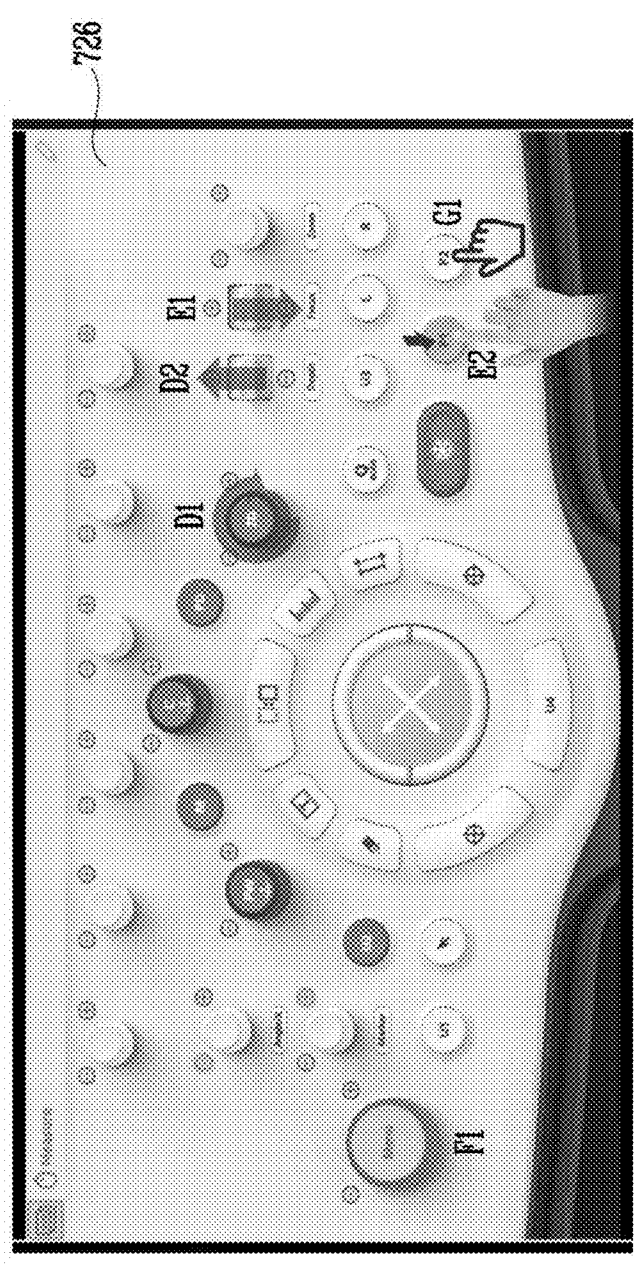
FIG. 15 is a diagram for explaining a display method of the ultrasound remote diagnosis system 700 in accordance with an embodiment of the present disclosure.

FIG. 15 is a diagram for explaining a display method of the ultrasound remote diagnosis system 700 in accordance with an embodiment of the present disclosure.

FIG. 15 is a diagram illustrating that a plurality of pieces of manipulation information are displayed on the second controller 726, and as an example of the manipulation information, it may be confirmed that a first manipulation by D1 and D2, a second manipulation by E1 and E2, a third manipulation by F1, and a fourth manipulation by G1 have been performed.

Each manipulation information is performed by the second controller 726 and the control panel 716, and as each manipulation information is displayed on the second controller 726 in a different display format, the user may confirm which manipulation was performed at a remote location or control panel.

Figure 16:
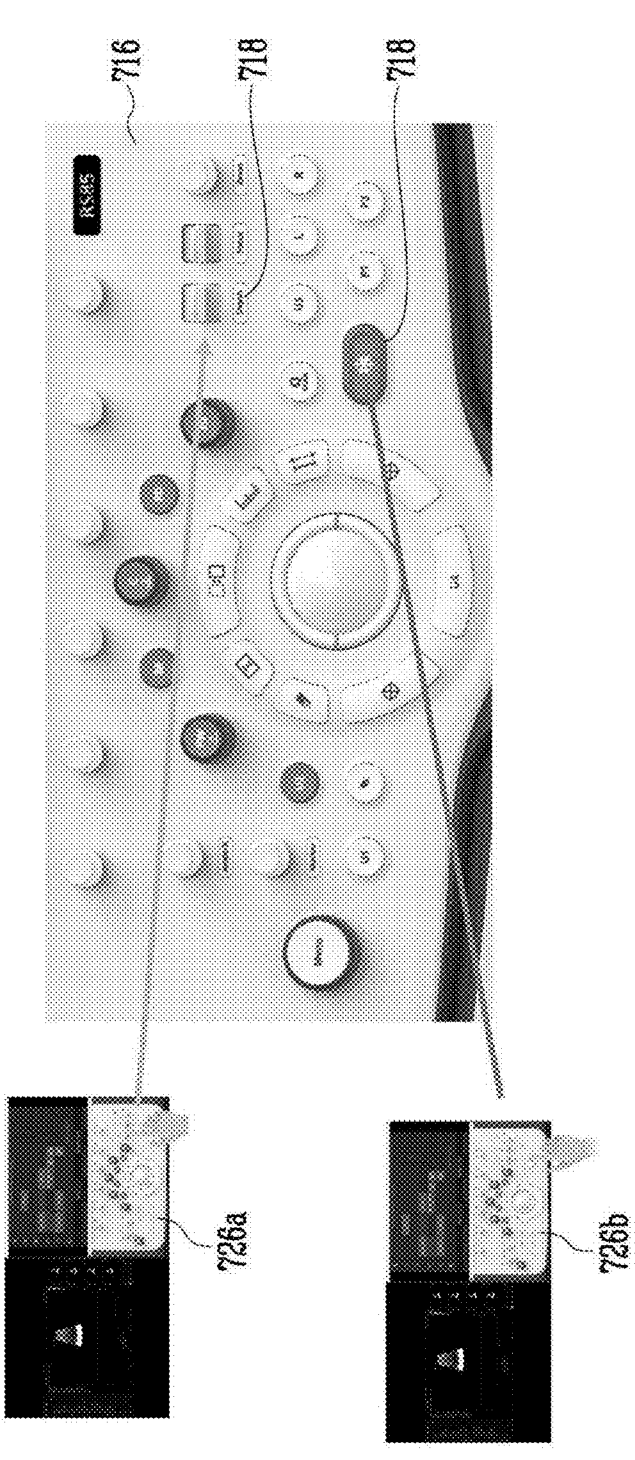
FIG. 16 is a diagram for explaining a display method of the ultrasound remote diagnosis system 700 in accordance with an embodiment of the present disclosure.

FIG. 16 is a diagram for explaining a display method of the ultrasound remote diagnosis system 700 in accordance with an embodiment of the present disclosure.

According to an embodiment of the present disclosure, manipulation information by the second controller 726 may be displayed on the control panel 716 in real time, and FIG. 16 illustrates an example of displaying information manipulated by each of the second controllers 726*a* and 726*b* on the control panel 716.

As illustrated in FIG. 16, manipulation information of the plurality of second controllers 726 may be displayed on the control panel 716, respectively, and manipulation information by the plurality of second controllers 726 displayed on the control panel 716 may be displayed in mutually distinguished forms.

According to an embodiment, the manipulation information displayed on the control panel 716 may be displayed in a blinking manner of the control panel manipulator 718.

The control panel manipulator 718 refers to configurations manipulated on the control panel 716, and although configurations manipulated by the second controllers 726*a* and 726*b* are displayed as a control panel manipulator 718 in FIG. 16, in addition to the configurations indicated as the control panel manipulator 718 in FIG. 16, the manipulation configuration on the control panel 716 may be the control panel manipulator 718.

In the control panel 716, a lightable LED is disposed on the button itself on the control panel 716, the switch, or its periphery, so whether or not it has been manipulated may be displayed by turning on the corresponding LED.

When the plurality of second controllers 726 are manipulated, the respective LED lighting colors may be different to distinguish them from each other. In addition, the manipulation information by the control panel 716 and manipulation information by the second controller 726, displayed on the control panel 716, may be displayed in mutually distinguished forms.

The ultrasound remote diagnosis method according to an embodiment of the present disclosure is an ultrasound remote diagnosis method of the ultrasound remote diagnosis system including a main body 710 including a main panel 712, a touch panel 714, and a control panel 716, and a remote device in communication with the main body 710.

The method includes independently receiving, by the remote device 720, among display data which is real-time image information of the main panel 712, first control data which is real-time image information of the touch panel 714, and second control data which is a virtual control panel corresponding to the control panel, at least each information corresponding to the display data and the first control data, from the main body 710, displaying, by the remote device 720, a display part 722, a first controller 724, and a second controller 726 respectively corresponding to the display data, the first control data, and the second control data so as not to overlap, and includes, in order for manipulation information by any one of the control panel 716 and the second controller 726 to be displayed on the other one, mutually transmitting the manipulation information between the main body 710 and the remote device 720.

According to an embodiment, displaying manipulation information by the control panel 716 on the second controller 726 in real time may be included, and displaying manipulation information by the second controller 726 on the control panel 716 in real time may be included.

Since detailed information related to each step has been sufficiently described in relation to the ultrasound remote diagnosis system 700 according to an embodiment of the present disclosure, a detailed description thereof will be omitted.

Hereinafter, a remote track ball 727 control method of an ultrasound remote diagnosis system 700 according to an embodiment of the present disclosure will be described.

Figure 17:
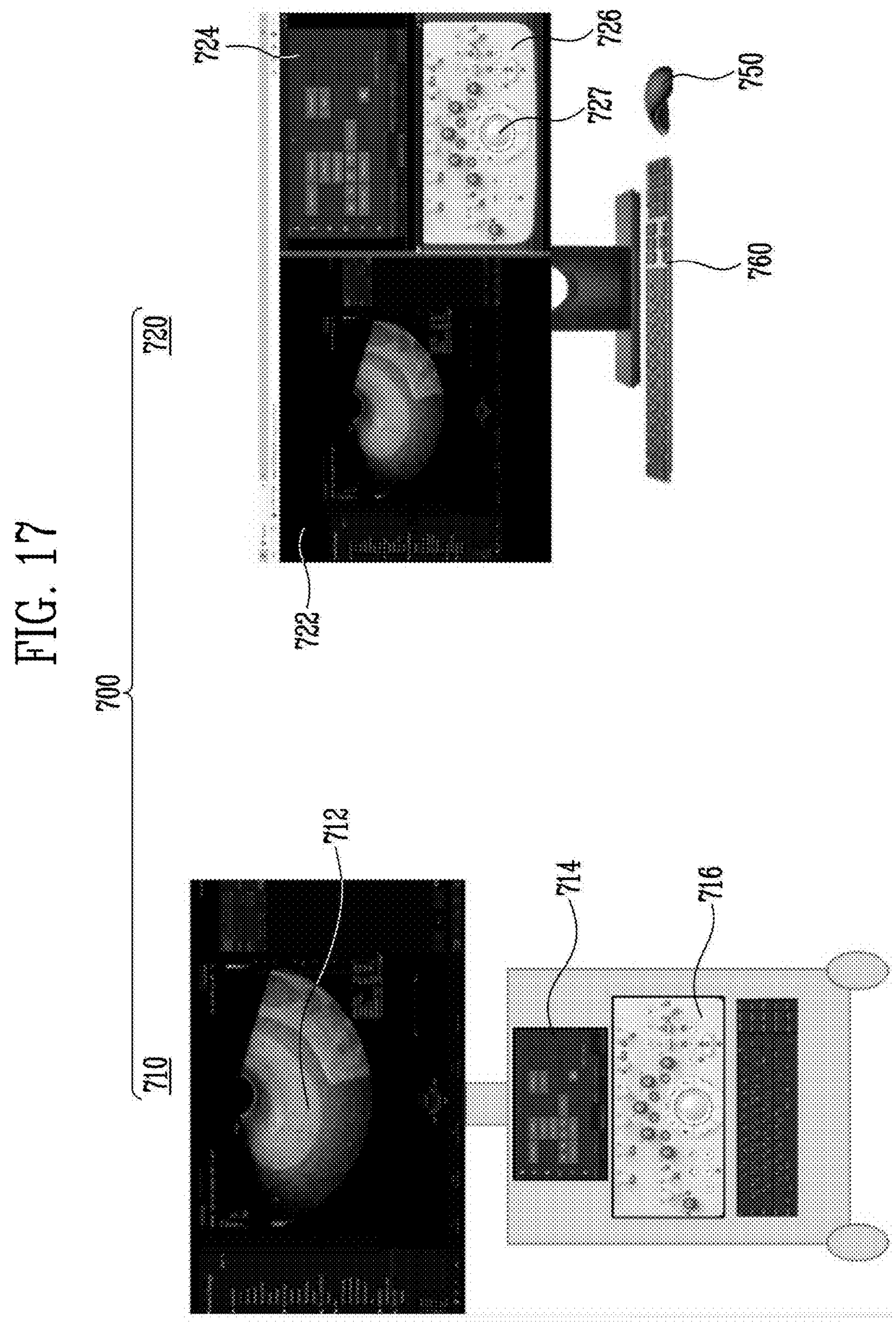
FIG. 17 is a diagram for explaining a remote track ball 727 control method of the ultrasound remote diagnosis system 700 in accordance with an embodiment of the present disclosure.

FIG. 17 is a diagram for explaining a remote track ball 727 control method of the ultrasound remote diagnosis system 700 in accordance with an embodiment of the present disclosure.

As illustrated in FIG. 17, the ultrasound remote diagnosis system 700 according to an embodiment of the present disclosure includes a main body 710 including a main panel 712, a touch panel 714, and a control panel 716, and a remote device 720 in communication with the main body 710.

The remote device 720 is configured to independently receive, among display data which is real-time image information of the main panel 712, first control data which is real-time image information of the touch panel 714, and second control data which is a virtual control panel corresponding to the control panel 716, at least each information corresponding to the display data and the first control data, from the main body 710, and display a display part 722, a first controller 724, and a second controller 726 respectively corresponding to the display data, the first control data, and the second control data so as not to overlap, and manipulation information of the remote track ball 727 is input by at least a part of the second controller 726 including the remote track ball 727 image or the periphery of the remote track ball 727 image.

According to another embodiment of the present disclosure, an ultrasound remote diagnosis system 700 includes a remote device 720 in communication with a main body 710 including a main panel 712, a touch panel 714, and a control panel 716, wherein the remote device 720 is configured to independently receive, among display data which is real-time image information of the main panel 712, first control data which is real-time image information of the touch panel 714, and second control data which is a virtual control panel corresponding to the control panel 716, at least each information corresponding to the display data and the first control data, from the main body 710, and display a display part 722, a first controller 724, and a second controller 726 respectively corresponding to the display data, the first control data, and the second control data so as not to overlap, wherein the second controller 726 includes a remote track ball 727 image corresponding to a track ball of the control panel 726, and manipulation information of the remote track ball 727 is input by at least a part of the second controller 726 including the remote track ball 727 image or a periphery of the remote track 727 ball image.

According to another embodiment of the present disclosure, an ultrasound remote diagnosis system 700 includes a main body 710 in communication with a remote device 720, wherein the main body 710 includes a main panel 712, a touch panel 714, and a control panel 716, and a remote device 720, in order for the remote device 720 to display a display part 722, a first controller 724, and a second controller 726 respectively corresponding to display data which is real-time image information of the main panel 712, first control data which is real-time image information of the touch panel 714, and second control data which is a virtual control panel corresponding to the control panel 716, so as not to overlap, and the main body 710 is configured to receive manipulation information of a remote track ball 727 input by at least a part of the second controller 726 including a remote track ball 727 image corresponding to a track ball of the control panel 716 or a remote track ball 727 image of the second controller 726.

A main body 710 in communication with a remote device 720 may be included, and the main body 710 may include a main panel 712, a touch panel 714, and a control panel 716, and a remote mouse 750 configured to control the remote track ball 727 of the second controller 726 may be included.

The first controller 724 may be controlled through the remote mouse 750, and the second controller 726 may be controlled through at least one of the remote mouse 750 and the remote keyboard 760.

In the ultrasound remote diagnosis system 700 of the present disclosure, the touch panel 714 and the first controller 724, the control panel 716 and the second controller 726 may each independently perform two-way transmission and reception, and at this time, the information transmitted from the first controller 724 to the touch panel 714 may include control information by the remote mouse 750 of the first controller 724, and the information transmitted from the second controller 726 to the control panel 716 may include control information by the remote mouse 750 and the remote keyboard 760 of the second controller 726.

Figure 18:
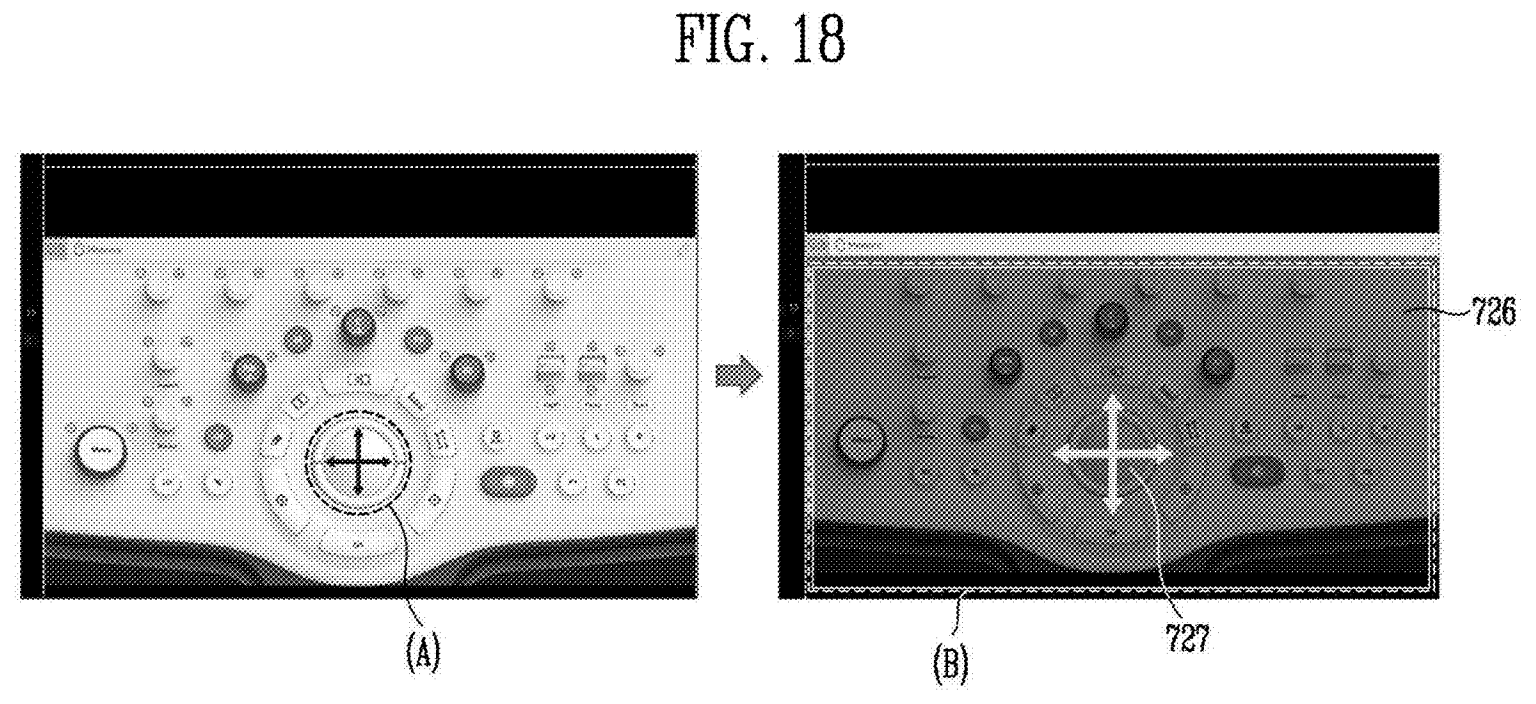

FIG. 18 is a diagram for explaining a method of controlling remote track ball 727, in a remote track ball 727 control method of the ultrasound remote diagnosis system 700 in accordance with the present disclosure.

First, in FIG. 18, the diagram shown on the left relates to a conventional ultrasound remote device. As a diagram illustrating the configuration of a remote location corresponding to a control panel of a conventional main body, as shown, in order to control the trackball on the control panel, the remote mouse could be moved only within the area A corresponding to the trackball. In other words, in the prior art, when the trackball is operated, the area that may be moved by the mouse at a remote location is narrow, which is inconvenient.

The diagram shown on the right side of FIG. 18 is a diagram illustrating the second controller 726 of the ultrasound remote diagnosis system 700 according to the present disclosure, and as shown, in the present disclosure, the remote mouse 750 may be moved within the entire area B of the second controller 726 to control the remote track ball 727.

In other words, in the present disclosure, as the movement area of the remote mouse 750 on the remote device 720 is within the area of the second controller 726, the movable range of the remote mouse 750 is widened compared to the prior art, so that there is an effect of facilitating the user's control of the remote trackball 727.

In addition, in order for the user to recognize that the remote mouse 750 may move to the second controller 726 beyond the remote track ball 727 area A, the second controller 726 of the present disclosure may indicate the movable area range of the remote mouse 750 in the shape of an arrow as shown in FIG. 18.

Depending on embodiments, it may be displayed on the main body 710 that the remote mouse 750 in a remote location is selected or operated.

Figure 19:
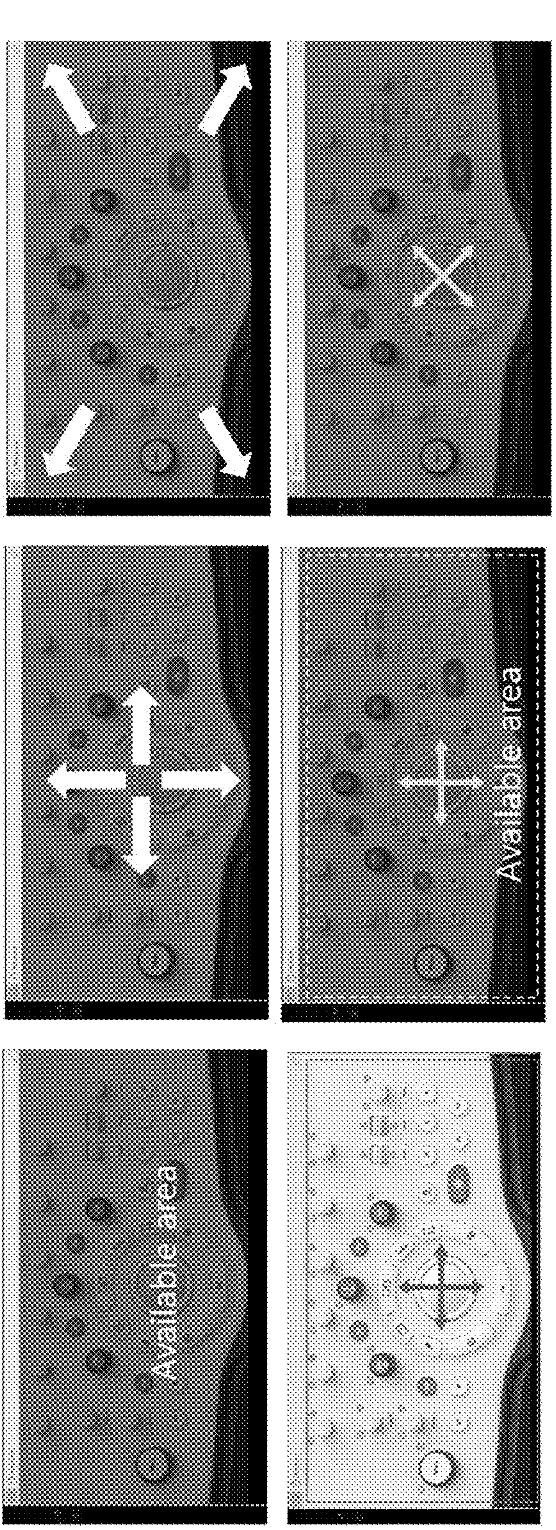
FIG. 19 is a diagram for explaining another embodiment in the remote track ball 727 control method of the ultrasound remote diagnosis system 700 in accordance with the present disclosure.

FIG. 19 is a diagram for explaining another embodiment, in a remote track ball 727 control method of the ultrasound remote diagnosis system 700 in accordance with the present disclosure.

As illustrated in FIG. 19, the second controller 726 in the present disclosure may be a movable area of the remote mouse 750 for controlling the remote track ball 727, and accordingly, FIG. 19 illustrates various embodiments for indicating that the entire second controller 726 is a movable area.

In the process of controlling the remote track ball 727, other buttons on the second controller 726 may not be used, and in order to notify the user of this, when the remote track ball 727 operates, the second controller 726 area may be shaded. In order to indicate that it is a movable area of the remote mouse 750 with shading, arrows may be displayed all over the second controller 726 up, down, left and right, the size of the arrows may be increased, or the direction of the arrows may be changed to point to both ends, and the available area may be indicated using text.

The method of indicating that it is a movable area is not limited to the above-listed methods or those illustrated in the drawings, and may be displayed in various ways by utilizing the color, transparency, text content, location, size, color, type of border line, color, etc., indicated by the second controller 726.

Figure 20A:
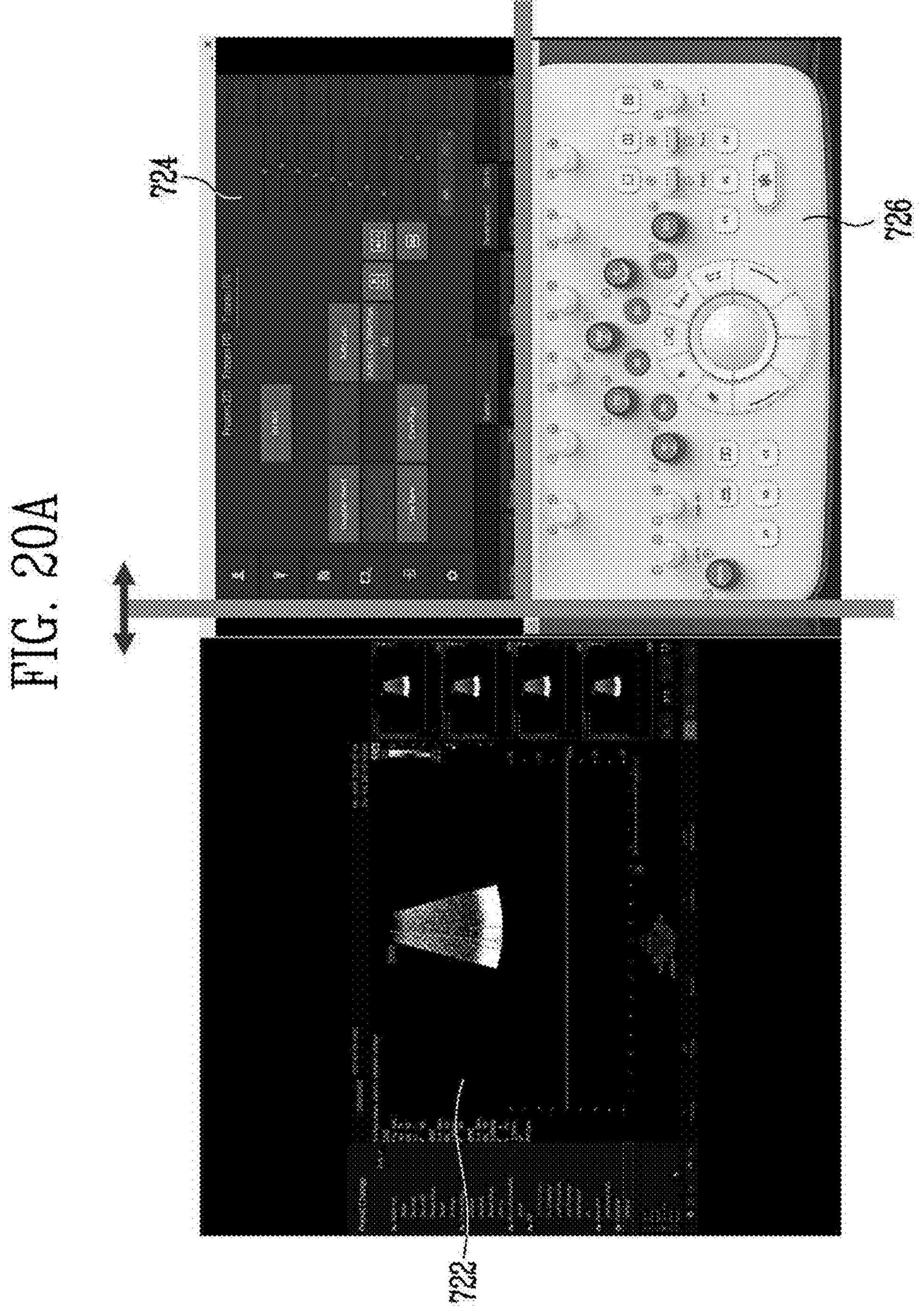
FIG. 20A is a diagram for explaining size control of a second controller 726, in the remote track ball 727 control method of the ultrasound remote diagnosis system 700 in accordance with an embodiment of the present disclosure.
Figure 20B:
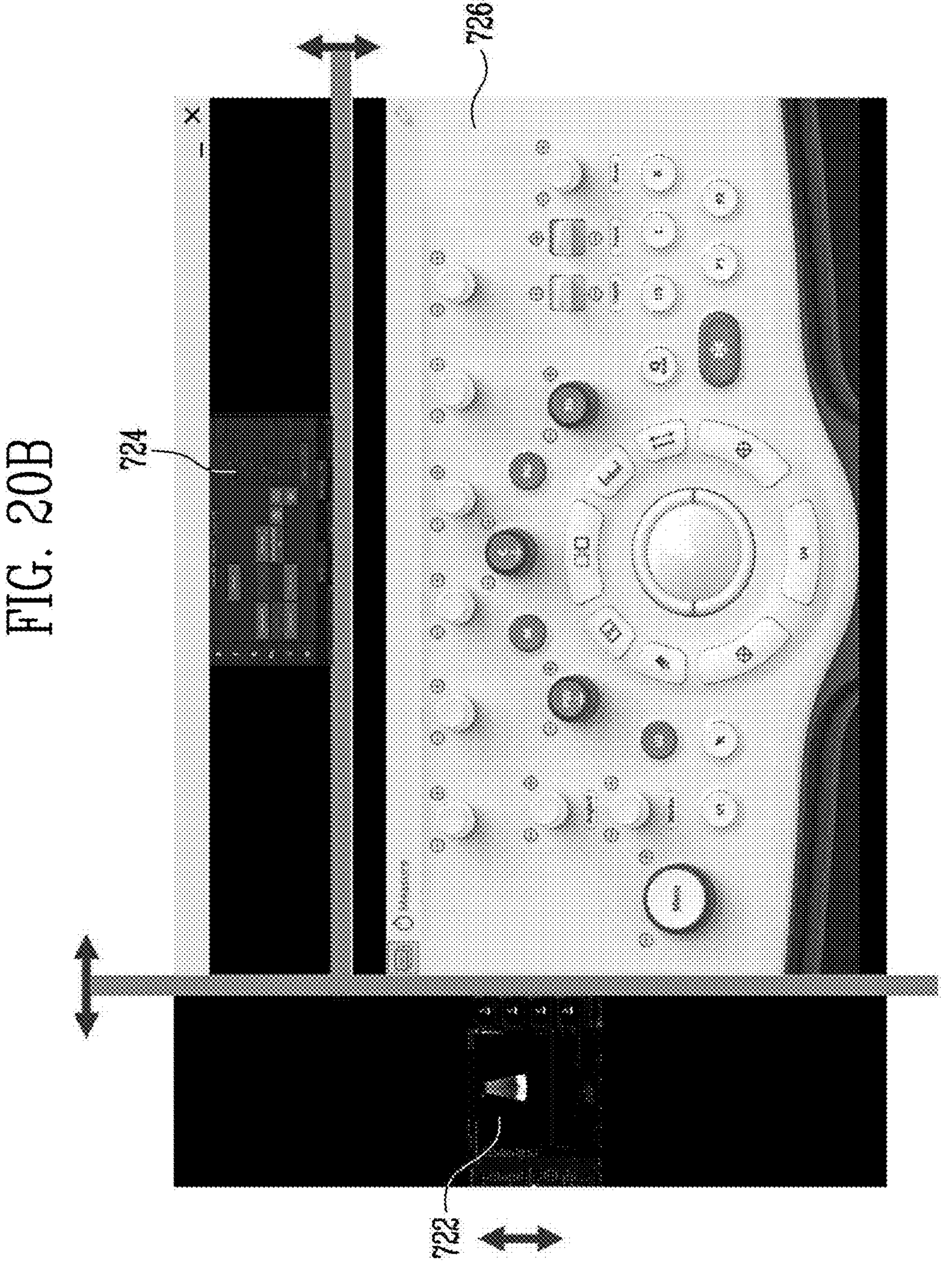
FIG. 20B is a diagram for explaining size control of the second controller 726, in the remote track ball 727 control method of the ultrasound remote diagnosis system 700 in accordance with an embodiment of the present disclosure.

FIG. 20A is a diagram for explaining size control of a second controller 726, in a remote track ball 727 control method of the ultrasound remote diagnosis system 700 in accordance with an embodiment of the present disclosure, and FIG. 20B is a diagram for explaining size control of a second controller 726, in the remote track ball 727 control method of the ultrasound remote diagnosis system 700 in accordance with an embodiment of the present disclosure.

The ultrasound remote diagnosis system 700 according to the present disclosure transmits information corresponding to the main panel 712, the touch panel 714, and the control panel 716 of the main body 710 as separate signals to the remote device 720, and on the remote device 720, the display part 722, the first controller 724, and the second controller 726 are displayed so as not to overlap each other, and their sizes may be independently controlled.

FIG. 20A illustrates the display part 722 on the left area of the remote device 720, the first controller 724 on the upper side of the right area, and the second controller 726 on the lower side, which illustrates a state in which the size ratio of both sides and the size ratio of the upper side and lower side are equally divided.

Contrary to this, FIG. 20B is a diagram illustrating a remote device 720 displayed by reducing the first controller 724 area at the upper side in order to enlarge the right area by reducing the size of the display part 722 in the left area, and further enlarge and display the second controller 726 at the lower side.

While in conventional ultrasound remote devices, as the information in the main body is integrated and transmitted as a single signal, independent control of each at a remote location was not possible, in the present disclosure, each size may be controlled independently, and only some windows in the display part 722, the first controller 724, and the second controller 726 may be closed or the size may be minimized.

Figure 21A:
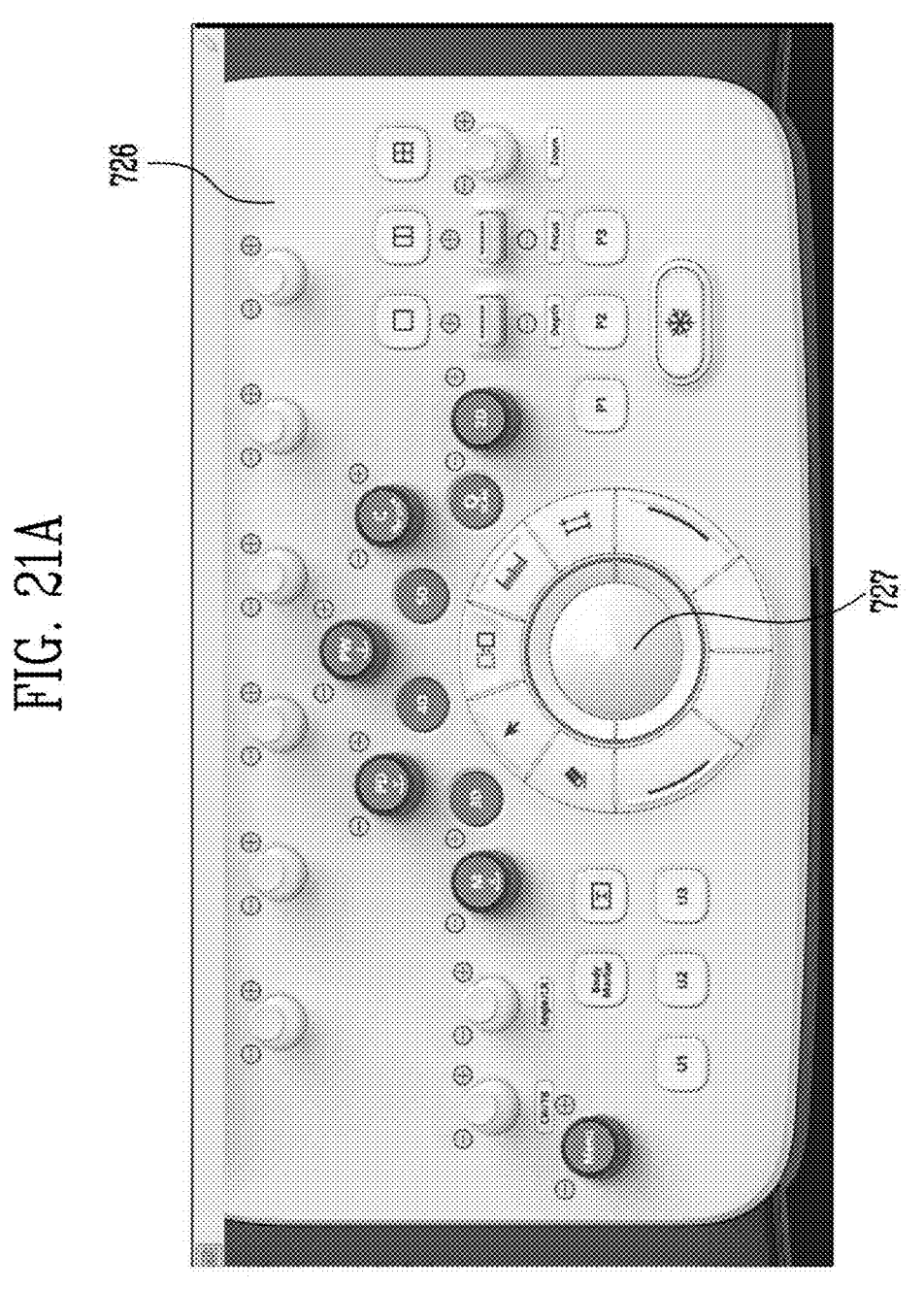
Figure 21B:
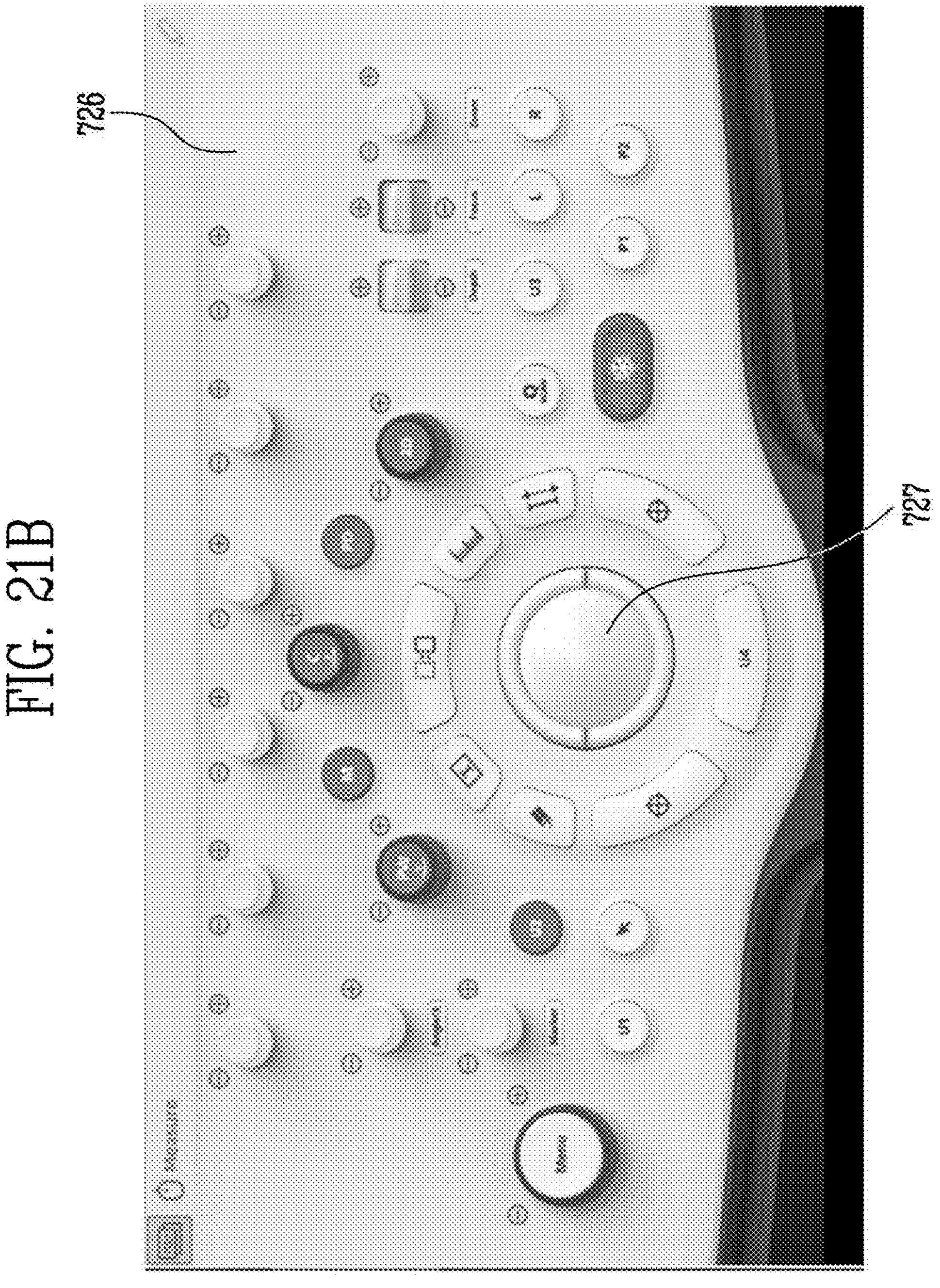
FIG. 21B is a diagram for explaining the second controller 726, in the remote track ball 727 control method of the ultrasound remote diagnosis system 700 in accordance with an embodiment of the present disclosure.

FIG. 21A is a diagram for explaining a second controller 726, in a remote track ball 727 control method of the ultrasound remote diagnosis system 700 in accordance with an embodiment of the present disclosure, and FIG. 21B is a diagram for explaining a second controller 726, in the remote track ball 727 control method of the ultrasound remote diagnosis system 700 in accordance with an embodiment of the present disclosure.

The second controller 726 in the present disclosure is a virtual control panel corresponding to the control panel 716 of the main body 710 and may have the same shape as the actual control panel 716 of the main body 710.

The second controller 726 illustrated in FIGS. 21A and 21B, illustrated as an example of the second controller 726, has different buttons provided on each, different functions by buttons, and slightly different shapes of buttons around the remote trackball 727.

As such, the second controller 726 displayed on the remote device 720 corresponds to the model of the control panel 716 of the main body 710, and model information and second control data of the control panel 716 may be previously stored in the ultrasound remote diagnosis system 700.

Figure 22:
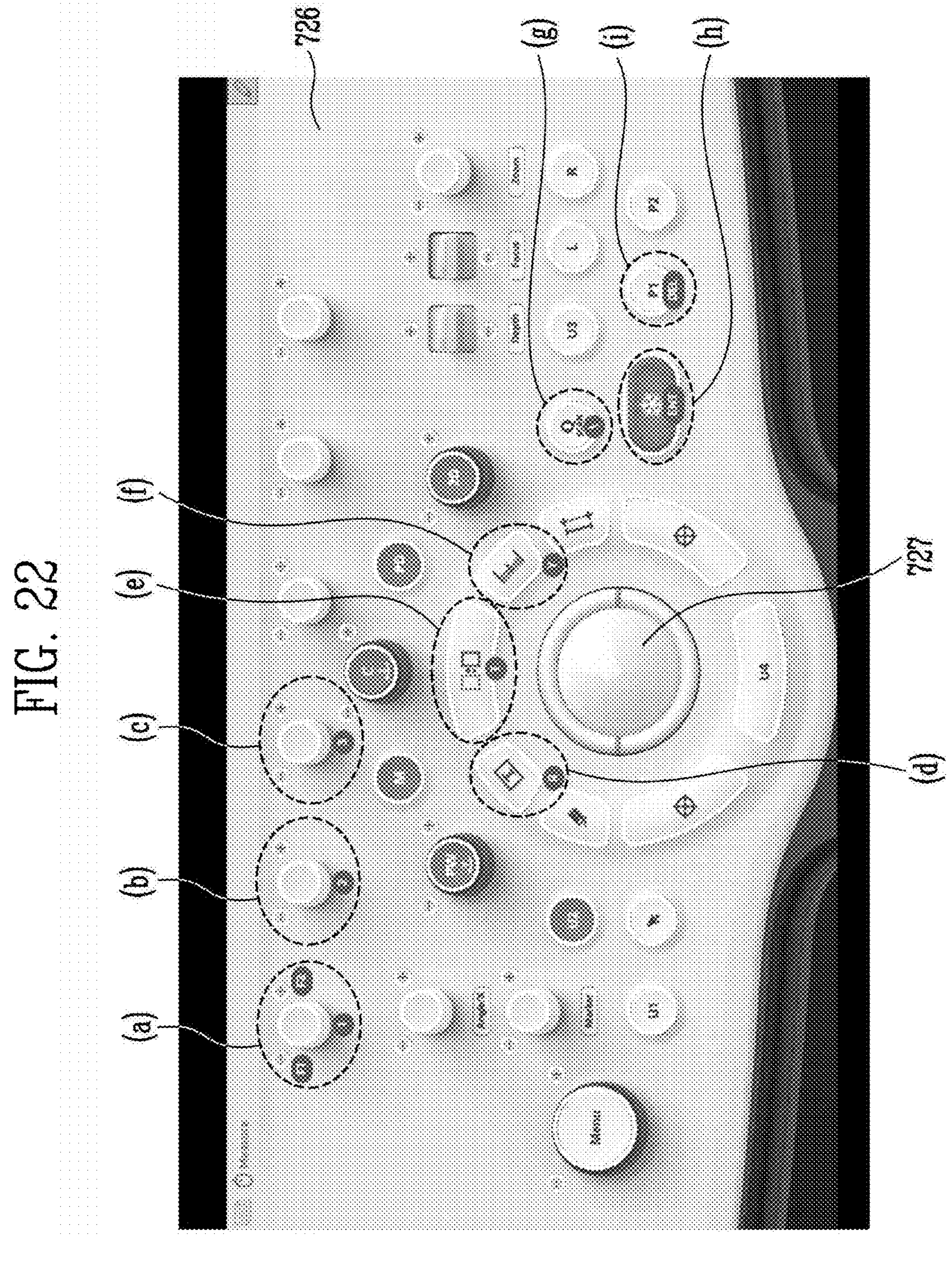
FIG. 22 is a diagram for explaining the second controller 726, in the remote track ball 727 control method of the ultrasound remote diagnosis system 700 in accordance with an embodiment of the present disclosure.

FIG. 22 is a diagram for explaining a second controller 726, in a remote track ball 727 control method of an ultrasound remote diagnosis system 700 in accordance with an embodiment of the present disclosure.

In the control method of he second controller 726, the user may set a shortcut key for controlling the second controller 726 on the remote keyboard 760.

Specifically, manipulation buttons and manipulation contents frequently used by the user in the second controller 726 may be designated to a specific key on the remote keyboard 760 in advance, and may be utilized as a shortcut key. There is an advantage in that the user's control becomes convenient in that it is performed only by pressing the key button of the remote keyboard 760 without the need to move the remote mouse 750.

FIG. 22 illustrates an example of a shortcut key, and in the case of configuration (a) of the second controller 726, the number 1 of the remote keyboard 760 is designated, and the – and + buttons are designated to F1 and F2 of the remote keyboard 760.

In the case of configuration (b), the number 2 of the remote keyboard 760 is designated, and in the configuration (c), the number 3 of the remote keyboard 760 is designated.

In the case of configuration (d), the alphabet R of the remote keyboard 760 is designated, in the case of configuration (e), the alphabet T of the remote keyboard 760 is designated, and in the configuration (f), the alphabet Y of the remote keyboard 760 is designated.

In addition, in configuration (g), the alphabet I of the remote keyboard 760 is designated, in configuration (h), the 'ENTER' key of the remote keyboard 760 is designated, and in the case of configuration (i), the 'DELETE' key of the remote keyboard 760 is designated.

FIG. 22 illustrates an example of a shortcut key, and in addition to the illustrated things, various shortcut keys corresponding to the remote keyboard 760 may be set in the configuration of the second controller 726 frequently used by the user.

The configuration illustrated in FIG. 22 illustrates an example of a shortcut key, and in addition to the illustrated things, various shortcut keys corresponding to the remote keyboard 760 may be set in the configuration of the second controller 726 frequently used by the user.

The remote keyboard 760 and the main body keyboard of the present disclosure may be mapped one-to-one.

However, if a shortcut key is set in the remote keyboard 760 as set above, the shortcut key set in the remote keyboard 760 may be preferentially applied in the remote keyboard 760, and in this case, the corresponding shortcut key may be effective only in a remote location.

The ultrasound remote diagnosis method according to an embodiment of the present disclosure is an ultrasound remote diagnosis method of the ultrasound remote diagnosis system including a main body 710 including a main panel 712, a touch panel 714, and a control panel 716, and a remote device in communication with the main body 710.

The method includes independently receiving, by the remote device 720, among display data which is real-time image information of the main panel 712, first control data which is real-time image information of the touch panel 714, and second control data which is a virtual control panel corresponding to the control panel, at least each information corresponding to the display data and the first control data, from the main body 710, displaying, by the remote device 720, a display part 722, a first controller 724, and a second controller 726 respectively corresponding to the display data, the first control data, and the second control data so as not to overlap, and while the second controller 726 includes a remote track ball 727 image corresponding to a track ball of the control panel 716, inputting manipulation information of the remote track ball 727 by at least a part of the second controller 726 including the remote track ball 727 image or a periphery of the remote track ball 727 image.

Since detailed information related to each step has been sufficiently described in relation to the ultrasound remote diagnosis system 700 according to an embodiment of the present disclosure, a detailed description thereof will be omitted.

The disclosed embodiments have been described with reference to the accompanying drawings as described above. Those skilled in the art to which the present disclosure pertains will understand that the present disclosure may be practiced in forms different from the disclosed embodiments without changing the technical spirit or essential features of the present disclosure. The disclosed embodiments are illustrative and should not be construed as limiting.

What is claimed is:

1. An ultrasound remote diagnosis system, comprising a main body for communicating with a remote device comprising a display, the main body comprising:

a main panel, a touch panel, and a control panel, wherein the control panel comprises at least one hardware button, wherein the main body is configured to:

display an ultrasound image on the main panel, in order for the remote device to display, in each of non-overlapping regions of the display of the remote device, a display part, a first controller, and a second controller respectively corresponding to display data which is real-time ultrasound image information of the main panel, first control data which is real-time image information of the touch panel, and second control data which is a virtual control panel information corresponding to the control panel, independently transmit, among the display data, the first control data and the second control data, at least each information corresponding to the display data and the second control data, to the remote device, wherein a button layout and a button function of the control panel of the main body correspond to a screen layout and a function of the second controller displayed on the remote device, wherein first manipulation information that is input via the control panel of the main body is displayed as a GUI (Graphic User Interface) on the second controller of the remote device in real time, by transmitting the first manipulation information from the main body to the remote device, wherein the first manipulation information comprises a button-input signal for the control panel generated by a user, and wherein second manipulation information that is input via the second controller of the remote device is displayed on the control panel of the main body in real time, by transmitting the second manipulation information from the remote device to the main body, wherein the second manipulation information comprises an input signal for a screen of the second controller generated by a user.

2. An ultrasound remote diagnosis system, comprising:

a main body comprising a main panel, a touch panel, and a control panel, wherein the control panel comprises at least one hardware button; and a remote device in communication with the main body comprising a display for displaying a display part, a first controller, and a second controller in each of non-overlapping regions of the display, wherein the remote device is configured to:

independently receive, among display data which is real-time ultrasound image information of the main panel, first control data which is real-time image information of the touch panel, and second control data which is a virtual control panel information corresponding to the control panel, at least each information corresponding to the display data and the second control data, from the main body; and display the display part, the first controller, and the second controller respectively corresponding to the display data, the first control data, and the second control data in each of non-overlapping regions of the display of the remote device, wherein a button layout and a button function of the control panel of the main body correspond to a screen layout and a function of the second controller displayed on the remote device, wherein first manipulation information that is input via the control panel of the main body is displayed as a GUI (Graphic User Interface) on the second controller of the remote device in real time, by transmitting the first manipulation information from the main body to the remote device, wherein the first manipulation information comprises a button-input signal for the control panel generated by a user, and wherein second manipulation information that is input via the second controller of the remote device is displayed on the control panel of the main body in real time, by transmitting the second manipulation information from the remote device to the main body, wherein the second manipulation information comprises an input signal for a screen of the second controller generated by a user.

3. The ultrasound remote diagnosis system of claim 1, wherein each of the first manipulation information by the control panel and the second manipulation information by the second controller is transmitted in two-way transmission and reception between the main body and the remote device, wherein the display data by the main panel is transmitted in one direction from the main panel of the main body to the display part of the remote device.

4. An ultrasound remote diagnosis method of an ultrasound remote diagnosis system comprising a main body comprising a main panel, a touch panel, and a control panel, and a remote device in communication with the main body, wherein the control panel comprises at least one hardware button, the ultrasound remote diagnosis method comprising:

independently receiving, by the remote device, among display data which is real-time ultrasound image information of the main panel, first control data which is real-time image information of the touch panel, and second control data which is a virtual control panel information corresponding to the control panel, at least each information corresponding to the display data and the second control data, from the main body; and displaying, by the remote device, a display part, a first controller, and a second controller respectively corresponding to the display data, the first control data, and the second control data in each of non-overlapping regions of a display of the remote device;

wherein a button layout and a button function of the control panel of the main body correspond to a screen layout and a function of the second controller displayed on the remote device, wherein first manipulation information that is input via the control panel of the main body is displayed as a GUI (Graphic User Interface) on the second controller of the remote device in real time, by transmitting the first manipulation information from the main body to the remote device, wherein the first manipulation information comprises a button-input signal for the control panel generated by a user, and wherein second manipulation information that is input via the second controller of the remote device is displayed on the control panel of the main body in real time, by transmitting the second manipulation information from the remote device to the main body, wherein the second manipulation information comprises an input signal for a screen of the second controller generated by a user.

5. The ultrasound remote diagnosis method of claim 4, further comprising:

receiving the first manipulation information via the at least one hardware button included in the control panel, and displaying the first manipulation information as at least one button GUI on the second controller in real time, wherein a shape of the at least one hardware button included in the control panel corresponds to a shape of the at least one button GUI displayed on the second controller.

6. The ultrasound remote diagnosis method of claim 4, wherein the remote device comprises a plurality of remote devices capable of remotely accessing the main body, each remote device comprising the second controller, wherein a plurality of pieces of second manipulation information respectively input via a plurality of second controllers included in the plurality of remote devices are transmitted from each of the plurality of remote devices to the main body, and wherein the plurality of pieces of second manipulation information are displayed in a different display format on the control panel, while the real-time ultrasound image information is displayed on the main panel of the main body.

7. The ultrasound remote diagnosis method of claim 6, wherein the plurality of pieces of second manipulation information of a plurality of the second controllers are respectively transmitted mutually between the plurality of second controllers, and wherein the plurality of pieces of manipulation information is displayed on each of the plurality of second controllers in mutually different display format.

8. The ultrasound remote diagnosis method of claim 4, wherein the second manipulation information displayed on the control panel, which is received from the remote device, is displayed in a blinking manner of a control panel manipulator, which comprises at least one of a button, a track ball, a jog switch, or a knob.

9. The ultrasound remote diagnosis method of claim 4, wherein the first manipulation information and the second manipulation information, displayed on the second controller in mutually different display format.

10. The ultrasound remote diagnosis method of claim 4, wherein each of the first manipulation information by the control panel and the second manipulation information by the second controller is transmitted in two-way transmission and reception between the main body and the remote device, and wherein the display data by the main panel is transmitted in one direction from the main panel of the main body to the display part of the remote device.

11. The ultrasound remote diagnosis system of claim 1, wherein each of the first manipulation information input via the control panel and the second manipulation information input via the second controller is displayed in a different display format on the control panel of the main body while the real-time ultrasound image information is displayed on the main panel of the main body.

12. The ultrasound remote diagnosis system of claim 2, wherein each of the first manipulation information input via the control panel and the second manipulation information input via the second controller is displayed in a different display format on the control panel of the main body while the real-time ultrasound image information is displayed on the main panel of the main body.

13. The ultrasound remote diagnosis method of claim 4, wherein each of the first manipulation information input via the control panel and the second manipulation information input via the second controller is displayed in a different display format on the control panel of the main body while the real-time ultrasound image information is displayed on the main panel of the main body.

* * * * *